(12) United States Patent
Rosinko et al.

(10) Patent No.: US 12,251,536 B2
(45) Date of Patent: *Mar. 18, 2025

(54) SYSTEM AND METHOD FOR INTEGRATION AND DISPLAY OF DATA OF INSULIN PUMPS AND CONTINUOUS GLUCOSE MONITORING

(71) Applicant: Tandem Diabetes Care, Inc., San Diego, CA (US)

(72) Inventors: Michael Rosinko, Anaheim, CA (US); Sean Saint, San Diego, CA (US); Jason Farnan, San Diego, CA (US); Shaun Buchanan, Carlsbad, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 136 days.

This patent is subject to a terminal disclaimer.

(21) Appl. No.: 18/108,902

(22) Filed: Feb. 13, 2023

(65) Prior Publication Data
US 2023/0191027 A1 Jun. 22, 2023

Related U.S. Application Data

(63) Continuation of application No. 16/590,836, filed on Oct. 2, 2019, now Pat. No. 11,607,492, which is a (Continued)

(51) Int. Cl.
*A61M 5/172* (2006.01)
*A61M 5/142* (2006.01)
*G16H 20/17* (2018.01)

(52) U.S. Cl.
CPC ...... *A61M 5/1723* (2013.01); *A61M 5/14244* (2013.01); *G16H 20/17* (2018.01);
(Continued)

(58) Field of Classification Search
CPC .............. A61M 5/1723; A61M 5/172; A61M 5/14244; A61M 2005/1726;
(Continued)

(56) References Cited

U.S. PATENT DOCUMENTS 2,462,596 A 2/1949 Bent
2,629,376 A 2/1953 Pierre et al.
(Continued)

FOREIGN PATENT DOCUMENTS

DE 399065 C 7/1924
DE 4407005 C1 3/1995
(Continued)

OTHER PUBLICATIONS

Application and File History for U.S. Appl. No. 13/800,453, filed Mar. 13, 2013, Inventors Rosinko.
(Continued)

*Primary Examiner* — Nathan R Price
*Assistant Examiner* — Adam J. Cermak
(74) *Attorney, Agent, or Firm* — Merchant & Gould P.C.

(57) ABSTRACT

A portable insulin pump can integrate and display data from a continuous glucose monitor (CGM) to allow a user to more readily determine whether any interaction with the pump is necessary. Data from the CGM can automatically be transmitted to the pump and can be displayed for user analysis or automatically analyzed to present recommendations to the user based on combined data from the CGM and the pump.

20 Claims, 8 Drawing Sheets

Related U.S. Application Data continuation of application No. 15/072,408, filed on Mar. 17, 2016, now abandoned, which is a continuation of application No. 13/800,453, filed on Mar. 13, 2013, now Pat. No. 10,357,606.

(52) U.S. Cl.
CPC . *A61M 2205/502* (2013.01); *A61M 2205/505* (2013.01); *A61M 2205/52* (2013.01); *A61M 2205/8206* (2013.01); *A61M 2230/201* (2013.01)

(58) Field of Classification Search
CPC ........ A61M 2205/52; A61M 2205/502; A61M 2205/505; A61M 2205/8206; A61M 2205/3592; A61M 2205/33; A61M 2230/201; A61B 5/14532; G16H 20/17; G16H 20/60; G06F 19/3468
See application file for complete search history.

(56) References Cited

U.S. PATENT DOCUMENTS

| | | | |
|---|---|---|---|
| 2,691,542 A | 10/1954 | Chenoweth | |
| 3,059,639 A | 10/1962 | Blackman et al. | |
| 4,393,365 A | 7/1983 | Kondo et al. | |
| 4,443,218 A | 4/1984 | DeCant, Jr. et al. | |
| 4,475,901 A | 10/1984 | Kraegen et al. | |
| 4,634,426 A | 1/1987 | Kamen | |
| 5,000,664 A | 3/1991 | Lawless et al. | |
| 5,050,612 A | 9/1991 | Matsumura | |
| 5,104,374 A | 4/1992 | Bishko | |
| 5,122,362 A | 6/1992 | Phillips et al. | |
| 5,148,154 A | 9/1992 | Mackay et al. | |
| 5,153,827 A | 10/1992 | Coutre et al. | |
| 5,181,910 A | 1/1993 | Scanlon | |
| 5,207,642 A | 5/1993 | Orkin et al. | |
| 5,219,330 A | 6/1993 | Bollish et al. | |
| 5,224,492 A | 7/1993 | Takahashi et al. | |
| 5,254,096 A | 10/1993 | Rondelet et al. | |
| 5,295,967 A | 3/1994 | Rondelet et al. | |
| 5,311,175 A | 5/1994 | Waldman | |
| 5,338,157 A | 8/1994 | Blomquist | |
| 5,339,393 A | 8/1994 | Duffy et al. | |
| 5,364,346 A | 11/1994 | Schrezenmeir | |
| 5,368,562 A | 11/1994 | Blomquist et al. | |
| 5,376,070 A | 12/1994 | Purvis et al. | |
| 5,389,078 A | 2/1995 | Zalesky et al. | |
| 5,395,326 A | 3/1995 | Haber et al. | |
| 5,438,510 A | 8/1995 | Bryant et al. | |
| 5,485,408 A | 1/1996 | Blomquist | |
| 5,569,186 A | 10/1996 | Lord et al. | |
| 5,658,250 A | 8/1997 | Blomquist et al. | |
| 5,658,252 A | 8/1997 | Johnson | |
| 5,665,065 A | 9/1997 | Colman et al. | |
| 5,669,877 A | 9/1997 | Blomquist | |
| 5,674,240 A | 10/1997 | Bonutti et al. | |
| 5,681,285 A | 10/1997 | Ford et al. | |
| 5,685,844 A | 11/1997 | Marttila | |
| 5,695,473 A | 12/1997 | Olsen | |
| 5,713,856 A | 2/1998 | Eggers et al. | |
| 5,782,805 A | 7/1998 | Meinzer et al. | |
| 5,810,771 A | 9/1998 | Blomquist | |
| 5,814,015 A * | 9/1998 | Gargano | A61M 5/1456 604/67 |
| 5,822,715 A | 10/1998 | Worthington et al. | |
| 5,839,356 A | 11/1998 | Dornbush et al. | |
| 5,876,370 A | 3/1999 | Blomquist | |
| 5,879,143 A | 3/1999 | Cote et al. | |
| 5,885,211 A | 3/1999 | Eppstein et al. | |
| 5,935,099 A | 8/1999 | Peterson et al. | |
| 5,935,106 A | 8/1999 | Olsen | |
| 6,023,629 A | 2/2000 | Tamada | |
| 6,024,539 A | 2/2000 | Blomquist | |
| 6,040,834 A | 3/2000 | Jain et al. | |
| 6,077,055 A | 6/2000 | Vilks | |
| 6,122,536 A | 9/2000 | Sun et al. | |
| 6,142,939 A | 11/2000 | Eppstein et al. | |
| 6,175,752 B1 | 1/2001 | Say et al. | |
| 6,225,999 B1 | 5/2001 | Jain et al. | |
| 6,229,584 B1 | 5/2001 | Chuo et al. | |
| 6,233,471 B1 | 5/2001 | Berner et al. | |
| 6,241,704 B1 | 6/2001 | Peterson et al. | |
| 6,248,057 B1 | 6/2001 | Mavity et al. | |
| 6,248,067 B1 | 6/2001 | Causey, III et al. | |
| 6,249,717 B1 | 6/2001 | Nicholson et al. | |
| 6,255,781 B1 | 7/2001 | Tsumura | |
| 6,269,340 B1 | 7/2001 | Ford et al. | |
| 6,272,364 B1 | 8/2001 | Kurnik | |
| 6,289,248 B1 | 9/2001 | Conley et al. | |
| 6,298,254 B2 | 10/2001 | Tamada | |
| D454,574 S | 3/2002 | Wasko et al. | |
| 6,368,272 B1 | 4/2002 | Porumbescu | |
| 6,422,057 B1 | 7/2002 | Anderson | |
| 6,475,180 B2 | 11/2002 | Peterson et al. | |
| 6,517,482 B1 | 2/2003 | Elden et al. | |
| 6,540,996 B1 | 4/2003 | Zwaal et al. | |
| 6,544,212 B2 | 4/2003 | Galley et al. | |
| 6,546,269 B1 | 4/2003 | Kurnik | |
| 6,551,276 B1 | 4/2003 | Mann et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,571,128 B2 | 5/2003 | Lebel et al. | |
| 6,577,323 B1 | 6/2003 | Jamieson et al. | |
| 6,577,899 B2 | 6/2003 | Lebel et al. | |
| 6,582,366 B1 | 6/2003 | Porumbescu | |
| 6,595,919 B2 | 7/2003 | Berner et al. | |
| 6,635,014 B2 | 10/2003 | Starkweather et al. | |
| 6,641,533 B2 | 11/2003 | Causey, III et al. | |
| 6,648,821 B2 | 11/2003 | Lebel et al. | |
| 6,668,196 B1 | 12/2003 | Villegas et al. | |
| 6,687,522 B2 | 2/2004 | Tamada | |
| 6,694,191 B2 | 2/2004 | Starkweather et al. | |
| 6,710,051 B1 | 3/2004 | Trier | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,771,250 B1 | 8/2004 | Oh | |
| 6,773,412 B2 | 8/2004 | O'Mahony et al. | |
| 6,790,198 B1 | 9/2004 | White et al. | |
| 6,809,653 B1 | 10/2004 | Mann et al. | |
| 6,810,290 B2 | 10/2004 | Lebel et al. | |
| 6,835,175 B1 | 12/2004 | Porumbescu | |
| 6,852,104 B2 | 2/2005 | Blomquist | |
| 6,872,200 B2 | 3/2005 | Mann et al. | |
| 6,873,268 B2 | 3/2005 | Lebel et al. | |
| 6,902,905 B2 | 6/2005 | Burson et al. | |
| 6,916,159 B2 | 7/2005 | Rush et al. | |
| 6,934,220 B1 | 8/2005 | Cruitt et al. | |
| 6,936,029 B2 | 8/2005 | Mann et al. | |
| 6,958,705 B2 | 10/2005 | Lebel et al. | |
| 6,974,437 B2 | 12/2005 | Lebel et al. | |
| 6,979,326 B2 | 12/2005 | Mann et al. | |
| 6,997,905 B2 | 2/2006 | Gillespie, Jr. et al. | |
| 6,997,920 B2 | 2/2006 | Mann et al. | |
| 6,998,387 B1 | 2/2006 | Goke et al. | |
| 7,025,743 B2 | 4/2006 | Mann et al. | |
| 7,033,338 B2 | 4/2006 | Vilks et al. | |
| 7,033,539 B2 | 4/2006 | Krensky et al. | |
| D521,521 S | 5/2006 | Jewitt et al. | |
| 7,041,082 B2 | 5/2006 | Blomquist et al. | |
| 7,098,803 B2 | 8/2006 | Mann et al. | |
| 7,109,878 B2 | 9/2006 | Mann et al. | |
| D531,637 S | 11/2006 | Chotai et al. | |
| 7,179,226 B2 | 2/2007 | Crothall et al. | |
| 7,183,068 B2 | 2/2007 | Burson et al. | |
| 7,204,823 B2 | 4/2007 | Estes et al. | |
| 7,231,263 B2 | 6/2007 | Choi | |
| 7,247,428 B2 | 7/2007 | Makrigiorgos | |
| 7,247,702 B2 | 7/2007 | Gardner et al. | |
| 7,267,665 B2 | 9/2007 | Steil et al. | |

(56) References Cited

U.S. PATENT DOCUMENTS

| | | |
|---|---|---|
| 7,278,983 B2 | 10/2007 | Ireland et al. |
| 7,291,107 B2 | 11/2007 | Hellwig et al. |
| 7,295,867 B2 | 11/2007 | Berner et al. |
| D557,272 S | 12/2007 | Glaser et al. |
| 7,307,245 B2 | 12/2007 | Faries, Jr. et al. |
| 7,324,012 B2 | 1/2008 | Mann et al. |
| 7,341,577 B2 | 3/2008 | Gill |
| 7,344,500 B2 | 3/2008 | Talbot et al. |
| 7,350,190 B2 | 3/2008 | Torres et al. |
| 7,404,796 B2 | 7/2008 | Ginsberg |
| 7,410,475 B2 | 8/2008 | Krensky et al. |
| 7,446,091 B2 | 11/2008 | Van Den Berghe |
| 7,464,010 B2 | 12/2008 | Yang et al. |
| 7,471,994 B2 | 12/2008 | Ford et al. |
| 7,491,187 B2 | 2/2009 | Van Den Berghe et al. |
| 7,497,827 B2 | 3/2009 | Brister et al. |
| 7,515,060 B2 | 4/2009 | Blomquist |
| 7,553,281 B2 | 6/2009 | Hellwig et al. |
| 7,559,926 B1 | 7/2009 | Blischak |
| 7,591,801 B2 | 9/2009 | Brauker et al. |
| 7,647,237 B2 | 1/2010 | Malave et al. |
| 7,651,489 B2 | 1/2010 | Estes et al. |
| 7,674,485 B2 | 3/2010 | Bhaskaran et al. |
| 7,678,071 B2 | 3/2010 | Lebel et al. |
| 7,678,762 B2 | 3/2010 | Green et al. |
| 7,678,763 B2 | 3/2010 | Green et al. |
| 7,711,402 B2 | 5/2010 | Shults et al. |
| 7,715,893 B2 | 5/2010 | Kamath et al. |
| 7,717,903 B2 | 5/2010 | Estes et al. |
| 7,727,148 B2 | 6/2010 | Talbot et al. |
| 7,734,323 B2 | 6/2010 | Blomquist et al. |
| 7,751,907 B2 | 7/2010 | Blomquist |
| 7,766,829 B2 | 8/2010 | Sloan et al. |
| 7,768,386 B2 | 8/2010 | Hayter et al. |
| 7,768,408 B2 | 8/2010 | Reggiardo et al. |
| 7,774,145 B2 | 8/2010 | Brauker et al. |
| 7,785,313 B2 | 8/2010 | Mastrototaro |
| 7,801,582 B2 | 9/2010 | Peyser |
| 7,806,886 B2 | 10/2010 | Kanderian, Jr. et al. |
| 7,831,287 B2 | 11/2010 | Brister et al. |
| 7,831,310 B2 | 11/2010 | Lebel et al. |
| 7,837,647 B2 | 11/2010 | Estes et al. |
| 7,869,851 B2 | 1/2011 | Hellwig et al. |
| 7,875,022 B2 | 1/2011 | Wenger et al. |
| 7,877,703 B1 | 1/2011 | Fleming |
| 7,884,729 B2 | 2/2011 | Reggiardo et al. |
| 7,912,674 B2 | 3/2011 | Killoren Clark et al. |
| 7,920,907 B2 | 4/2011 | McGarraugh et al. |
| 7,935,105 B2 | 5/2011 | Miller et al. |
| 7,941,200 B2 | 5/2011 | Weinert et al. |
| 7,942,844 B2 | 5/2011 | Moberg et al. |
| 7,945,452 B2 | 5/2011 | Fathallah et al. |
| 7,946,985 B2 | 5/2011 | Mastrototaro et al. |
| 7,951,114 B2 | 5/2011 | Rush et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,979,136 B2 | 7/2011 | Young et al. |
| 7,985,330 B2 | 7/2011 | Wang et al. |
| 7,988,850 B2 | 8/2011 | Roncadi et al. |
| 7,996,158 B2 | 8/2011 | Hayter et al. |
| 8,012,119 B2 | 9/2011 | Estes et al. |
| 8,032,226 B2 | 10/2011 | Miller et al. |
| 8,062,249 B2 | 11/2011 | Wilinska et al. |
| 8,066,665 B2 | 11/2011 | Rush et al. |
| 8,075,527 B2 | 12/2011 | Rush et al. |
| 8,078,983 B2 | 12/2011 | Davis et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,093,212 B2 | 1/2012 | Gardner et al. |
| 8,109,921 B2 | 2/2012 | Estes et al. |
| 8,114,066 B2 | 2/2012 | Naef et al. |
| 8,114,350 B1 | 2/2012 | Silver et al. |
| 8,119,593 B2 | 2/2012 | Richardson et al. |
| 8,121,689 B2 | 2/2012 | Kalgren et al. |
| 8,127,046 B2 | 2/2012 | Grant et al. |
| 8,129,429 B2 | 3/2012 | Sporn et al. |
| 8,133,197 B2 | 3/2012 | Blomquist et al. |
| 8,140,312 B2 | 3/2012 | Hayter et al. |
| 8,147,446 B2 | 4/2012 | Yodfat et al. |
| 8,152,789 B2 | 4/2012 | Starkweather et al. |
| D660,317 S | 5/2012 | Jesberger |
| 8,192,394 B2 | 6/2012 | Estes et al. |
| 8,204,729 B2 | 6/2012 | Sher |
| 8,208,984 B2 | 6/2012 | Blomquist et al. |
| 8,211,093 B2 | 7/2012 | Miller et al. |
| 8,219,222 B2 | 7/2012 | Blomquist |
| 8,221,345 B2 | 7/2012 | Blomquist |
| 8,234,128 B2 | 7/2012 | Martucci et al. |
| D664,982 S | 8/2012 | Rai et al. |
| D665,407 S | 8/2012 | Bitran et al. |
| 8,237,715 B2 | 8/2012 | Buck et al. |
| 8,246,540 B2 | 8/2012 | Ginsberg |
| 8,250,483 B2 | 8/2012 | Blomquist |
| 8,251,906 B2 | 8/2012 | Brauker et al. |
| D667,022 S | 9/2012 | LoBosco et al. |
| 8,257,259 B2 | 9/2012 | Brauker et al. |
| 8,257,300 B2 | 9/2012 | Budiman et al. |
| 8,287,495 B2 | 10/2012 | Michaud et al. |
| 8,287,514 B2 | 10/2012 | Miller et al. |
| 8,310,415 B2 | 11/2012 | McLaughlin et al. |
| 8,311,749 B2 | 11/2012 | Brauker et al. |
| 8,317,752 B2 | 11/2012 | Cozmi et al. |
| 8,337,469 B2 | 12/2012 | Eberhart et al. |
| 8,344,847 B2 | 1/2013 | Moberg et al. |
| 8,348,885 B2 | 1/2013 | Moberg et al. |
| 8,369,919 B2 | 2/2013 | Kamath et al. |
| 8,372,040 B2 | 2/2013 | Huang et al. |
| 8,395,581 B2 | 3/2013 | Graskov et al. |
| 8,402,145 B2 | 3/2013 | Holden et al. |
| 8,414,563 B2 | 4/2013 | Kamen et al. |
| 8,452,413 B2 | 5/2013 | Young |
| 8,454,510 B2 | 6/2013 | Yodfat et al. |
| 8,454,576 B2 | 6/2013 | Mastrototaro et al. |
| 8,460,231 B2 | 6/2013 | Brauker et al. |
| D691,632 S | 10/2013 | Impas |
| 8,552,880 B2 | 10/2013 | Kopp et al. |
| 8,562,558 B2 | 10/2013 | Kamath et al. |
| D694,253 S | 11/2013 | Helm |
| 8,573,027 B2 | 11/2013 | Rosinko et al. |
| 8,601,561 B1 * | 12/2013 | Cleron ............... G06F 3/04886 726/7 |
| 8,650,937 B2 | 2/2014 | Brown |
| 8,657,779 B2 | 2/2014 | Blomquist |
| 8,710,993 B2 | 4/2014 | Hayter et al. |
| 8,712,748 B2 | 4/2014 | Thukral et al. |
| D707,705 S | 6/2014 | Folken et al. |
| 8,777,895 B2 | 7/2014 | Hsu |
| 8,818,782 B2 | 8/2014 | Thukral |
| D712,920 S | 9/2014 | Sloo et al. |
| D715,315 S | 10/2014 | Wood |
| 8,882,701 B2 | 11/2014 | DeBelser et al. |
| 8,929,823 B2 | 1/2015 | Mears et al. |
| 8,938,306 B2 | 1/2015 | Lebel et al. |
| 8,985,253 B2 | 3/2015 | Winter et al. |
| 8,986,253 B2 | 3/2015 | DiPerna |
| D727,337 S | 4/2015 | Kim et al. |
| 9,008,803 B2 | 4/2015 | Blomquist |
| 9,037,254 B2 | 5/2015 | John |
| D731,529 S | 6/2015 | Cavander et al. |
| D739,872 S | 9/2015 | Bang et al. |
| D745,020 S | 12/2015 | Mariet et al. |
| D746,849 S | 1/2016 | Anzures et al. |
| 9,238,100 B2 | 1/2016 | Kruse et al. |
| D748,644 S | 2/2016 | Huang |
| D754,181 S | 4/2016 | Dong et al. |
| D754,690 S | 4/2016 | Park et al. |
| D755,223 S | 5/2016 | Liu et al. |
| D757,032 S | 5/2016 | Sabia et al. |
| 9,335,910 B2 | 5/2016 | Farnan et al. |
| D759,687 S | 6/2016 | Chang et al. |
| 9,364,679 B2 | 6/2016 | John |

(56) References Cited

U.S. PATENT DOCUMENTS

| | | |
|---|---|---|
| D761,843 S | 7/2016 | Kim |
| 9,381,297 B2 | 7/2016 | Brown |
| 9,381,302 B2 | 7/2016 | Miller |
| 9,400,241 B2 | 7/2016 | Brown |
| D763,267 S | 8/2016 | Brunner et al. |
| D765,099 S | 8/2016 | Kim et al. |
| D767,605 S | 9/2016 | Mensinger et al. |
| D770,519 S | 11/2016 | Kobetz et al. |
| D771,086 S | 11/2016 | Kim et al. |
| D771,650 S | 11/2016 | Yang |
| D771,690 S | 11/2016 | Yin et al. |
| 9,483,615 B2 | 11/2016 | Roberts |
| 9,486,171 B2 | 11/2016 | Saint |
| 9,486,578 B2 | 11/2016 | Finan et al. |
| D773,534 S | 12/2016 | Yuk et al. |
| D774,078 S | 12/2016 | Kisselev et al. |
| D775,184 S | 12/2016 | Song et al. |
| D784,401 S | 4/2017 | Joi |
| D789,417 S | 6/2017 | Yamasaki et al. |
| D789,968 S | 6/2017 | Mensinger et al. |
| 9,669,160 B2 | 6/2017 | Harris |
| 9,675,756 B2 | 6/2017 | Kamen |
| 9,715,327 B2 | 7/2017 | Rosinko et al. |
| D794,650 S | 8/2017 | Lee et al. |
| D798,895 S | 10/2017 | Kim et al. |
| 9,814,835 B2 | 11/2017 | Kruse et al. |
| 9,833,177 B2 | 12/2017 | Blomquist |
| D808,990 S | 1/2018 | Ayvazian et al. |
| D808,998 S | 1/2018 | Wu et al. |
| 9,867,937 B2 | 1/2018 | Saint et al. |
| 9,867,953 B2 | 1/2018 | Rosinko |
| 9,942,091 B2 | 4/2018 | Harvey et al. |
| 9,970,893 B2 | 5/2018 | Morgan |
| 9,974,903 B1 | 5/2018 | Davis et al. |
| D820,283 S | 6/2018 | Cabrera, Jr. et al. |
| D820,302 S | 6/2018 | Choi et al. |
| D822,695 S | 7/2018 | Iketsuki et al. |
| 10,016,561 B2 | 7/2018 | Saint et al. |
| 10,035,065 B2 | 7/2018 | Schupak et al. |
| 10,052,049 B2 | 8/2018 | Blomquist et al. |
| D831,049 S | 10/2018 | Agarwal et al. |
| D834,594 S | 11/2018 | Anzures et al. |
| D836,131 S | 12/2018 | Apodaca et al. |
| 10,213,547 B2 | 2/2019 | Rosinko |
| D844,643 S | 4/2019 | Cabrera, Jr. et al. |
| D847,169 S | 4/2019 | Sombreireiro et al. |
| D849,036 S | 5/2019 | Fuller et al. |
| D851,112 S | 6/2019 | Papolu et al. |
| D852,809 S | 7/2019 | Rad et al. |
| D852,811 S | 7/2019 | Babion |
| 10,357,606 B2 * | 7/2019 | Rosinko .............. A61M 5/1723 |
| 10,357,607 B2 | 7/2019 | Blomquist et al. |
| D858,535 S | 9/2019 | Evans et al. |
| D864,218 S | 10/2019 | Farnan et al. |
| D864,219 S | 10/2019 | Farnan et al. |
| 10,430,043 B2 | 10/2019 | Rosinko et al. |
| 10,434,253 B2 | 10/2019 | Diperna et al. |
| D865,778 S | 11/2019 | Kim et al. |
| 10,549,051 B2 | 2/2020 | Rosinko |
| 10,569,016 B2 | 2/2020 | Rosinko |
| 10,653,834 B2 | 5/2020 | Kruse et al. |
| 10,864,322 B2 | 12/2020 | Saint et al. |
| 11,607,492 B2 * | 3/2023 | Rosinko ................ G16H 20/17 |
| 2001/0001144 A1 | 5/2001 | Kapp |
| 2001/0027791 A1 | 10/2001 | Wallace et al. |
| 2001/0031944 A1 | 10/2001 | Peterson et al. |
| 2001/0037217 A1 | 11/2001 | Abensour et al. |
| 2001/0041831 A1 | 11/2001 | Starkweather et al. |
| 2002/0002326 A1 | 1/2002 | Causey, III et al. |
| 2002/0016568 A1 | 2/2002 | Lebel |
| 2002/0019606 A1 | 2/2002 | Lebel |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0050621 A1 | 3/2003 | Lebel et al. |
| 2003/0060765 A1 | 3/2003 | Campbell et al. |
| 2003/0065308 A1 | 4/2003 | Lebel et al. |
| 2003/0114836 A1 | 6/2003 | Estes et al. |
| 2003/0130616 A1 | 7/2003 | Steil et al. |
| 2003/0145854 A1 | 8/2003 | Hickle |
| 2003/0159945 A1 | 8/2003 | Miyazaki et al. |
| 2003/0160683 A1 | 8/2003 | Blomquist |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163789 A1 | 8/2003 | Blomquist |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0015102 A1 | 1/2004 | Cummings et al. |
| 2004/0015132 A1 | 1/2004 | Brown |
| 2004/0068230 A1 | 4/2004 | Estes et al. |
| 2004/0073095 A1 | 4/2004 | Causey, III et al. |
| 2004/0115067 A1 | 6/2004 | Rush et al. |
| 2004/0122353 A1 | 6/2004 | Shahmirian et al. |
| 2004/0152622 A1 | 8/2004 | Keith et al. |
| 2004/0172222 A1 | 9/2004 | Simpson |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0225252 A1 | 11/2004 | Gillespie et al. |
| 2004/0254434 A1 | 12/2004 | Goodnow et al. |
| 2005/0021006 A1 | 1/2005 | Tonnies |
| 2005/0022274 A1 | 1/2005 | Campbell et al. |
| 2005/0027182 A1 | 2/2005 | Siddiqui et al. |
| 2005/0030164 A1 | 2/2005 | Blomquist |
| 2005/0065464 A1 | 3/2005 | Talbot et al. |
| 2005/0065760 A1 | 3/2005 | Murtfeldt et al. |
| 2005/0081847 A1 | 4/2005 | Lee et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0171513 A1 | 8/2005 | Mann et al. |
| 2005/0182358 A1 | 8/2005 | Veit et al. |
| 2005/0182831 A1 | 8/2005 | Uchida et al. |
| 2005/0192557 A1 | 9/2005 | Brauker et al. |
| 2005/0197553 A1 | 9/2005 | Cooper |
| 2005/0197621 A1 | 9/2005 | Poulsen et al. |
| 2005/0228234 A1 | 10/2005 | Yang |
| 2005/0272640 A1 | 12/2005 | Doyle, III et al. |
| 2005/0277872 A1 | 12/2005 | Colby, Jr. et al. |
| 2005/0277912 A1 | 12/2005 | John |
| 2006/0001538 A1 | 1/2006 | Kraft et al. |
| 2006/0001550 A1 | 1/2006 | Mann et al. |
| 2006/0014670 A1 | 1/2006 | Green et al. |
| 2006/0031094 A1 | 2/2006 | Cohen et al. |
| 2006/0047192 A1 | 3/2006 | Hellwig et al. |
| 2006/0047538 A1 | 3/2006 | Condurso et al. |
| 2006/0073891 A1 | 4/2006 | Holt |
| 2006/0080059 A1 | 4/2006 | Stupp et al. |
| 2006/0085223 A1 | 4/2006 | Anderson et al. |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1 | 10/2006 | Steil et al. |
| 2006/0229557 A1 * | 10/2006 | Fathallah ............... G16H 40/63 705/2 |
| 2006/0253097 A1 | 11/2006 | Braig et al. |
| 2006/0264895 A1 | 11/2006 | Flanders |
| 2006/0271020 A1 | 11/2006 | Huang et al. |
| 2006/0272652 A1 | 12/2006 | Stocker et al. |
| 2006/0276771 A1 | 12/2006 | Galley et al. |

(56) References Cited

U.S. PATENT DOCUMENTS

| | | |
|---|---|---|
| 2007/0016127 A1 | 1/2007 | Staib et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0066956 A1 | 3/2007 | Finkel |
| 2007/0083152 A1 | 4/2007 | Williams et al. |
| 2007/0083335 A1 | 4/2007 | Moerman |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0112298 A1 | 5/2007 | Mueller et al. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0156457 A1 | 7/2007 | Brown |
| 2007/0173712 A1 | 7/2007 | Shah et al. |
| 2007/0203454 A1 | 8/2007 | Shermer et al. |
| 2007/0213657 A1 | 9/2007 | Jennewine et al. |
| 2007/0233051 A1 | 10/2007 | Hohl et al. |
| 2007/0245258 A1 | 10/2007 | Ginggen et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0287985 A1 | 12/2007 | Estes et al. |
| 2007/0299389 A1 | 12/2007 | Halbert et al. |
| 2008/0004601 A1 | 1/2008 | Jennewine et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0059158 A1 | 3/2008 | Matsuo et al. |
| 2008/0065007 A1 | 3/2008 | Peterson et al. |
| 2008/0065016 A1 | 3/2008 | Peterson et al. |
| 2008/0071209 A1 | 3/2008 | Moubayed et al. |
| 2008/0071210 A1 | 3/2008 | Moubayed et al. |
| 2008/0071217 A1 | 3/2008 | Moubayed et al. |
| 2008/0071251 A1 | 3/2008 | Moubayed et al. |
| 2008/0071580 A1 | 3/2008 | Marcus et al. |
| 2008/0076969 A1 | 3/2008 | Kraft et al. |
| 2008/0097289 A1 | 4/2008 | Steil et al. |
| 2008/0106431 A1 | 5/2008 | Blomquist |
| 2008/0114299 A1 | 5/2008 | Damgaard-Sorensen et al. |
| 2008/0132844 A1 | 6/2008 | Peterson et al. |
| 2008/0139907 A1 | 6/2008 | Rao et al. |
| 2008/0147004 A1 | 6/2008 | Mann et al. |
| 2008/0147050 A1 | 6/2008 | Mann et al. |
| 2008/0148235 A1 | 6/2008 | Foresti et al. |
| 2008/0154513 A1 | 6/2008 | Kovatchev et al. |
| 2008/0156661 A1 | 7/2008 | Cooper et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0200868 A1 | 8/2008 | Alberti et al. |
| 2008/0206799 A1 | 8/2008 | Blomquist |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2008/0300572 A1 | 12/2008 | Rankers et al. |
| 2008/0306434 A1 | 12/2008 | Dobbles et al. |
| 2008/0306444 A1 | 12/2008 | Brister et al. |
| 2008/0312584 A1 | 12/2008 | Montgomery et al. |
| 2008/0312585 A1 | 12/2008 | Brukalo et al. |
| 2009/0006061 A1 | 1/2009 | Thukral |
| 2009/0006129 A1 | 1/2009 | Thukral et al. |
| 2009/0018495 A1 | 1/2009 | Panduro |
| 2009/0058598 A1 | 3/2009 | Sanchez Sanchez et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069785 A1 | 3/2009 | Miller et al. |
| 2009/0069787 A1 | 3/2009 | Estes et al. |
| 2009/0088731 A1 | 4/2009 | Campbell et al. |
| 2009/0093756 A1 | 4/2009 | Minaie et al. |
| 2009/0099866 A1 | 4/2009 | Newman |
| 2009/0099867 A1 | 4/2009 | Newman |
| 2009/0105636 A1 | 4/2009 | Hayter et al. |
| 2009/0105646 A1 | 4/2009 | Hendrixson et al. |
| 2009/0113295 A1 | 4/2009 | Halpern et al. |
| 2009/0131860 A1 | 5/2009 | Nielsen |
| 2009/0150484 A1 | 6/2009 | Roberts |
| 2009/0156990 A1 | 6/2009 | Wenger et al. |
| 2009/0156991 A1 | 6/2009 | Roberts |
| 2009/0157202 A1 | 6/2009 | Roberts et al. |
| 2009/0157622 A1 | 6/2009 | Roberts et al. |
| 2009/0157695 A1 | 6/2009 | Roberts |
| 2009/0158274 A1 | 6/2009 | Roberts |
| 2009/0163855 A1 | 6/2009 | Shin et al. |
| 2009/0167717 A1 | 7/2009 | Wang et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba, Jr. et al. |
| 2009/0177248 A1 | 7/2009 | Roberts |
| 2009/0177249 A1 | 7/2009 | Roberts et al. |
| 2009/0177769 A1 | 7/2009 | Roberts |
| 2009/0177991 A1 | 7/2009 | Davis et al. |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0204341 A1 | 8/2009 | Brauker et al. |
| 2009/0212966 A1 | 8/2009 | Panduro |
| 2009/0216100 A1 | 8/2009 | Ebner et al. |
| 2009/0221890 A1* | 9/2009 | Saffer .................. A61B 5/742 600/347 |
| 2009/0240193 A1 | 9/2009 | Mensinger et al. |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0270833 A1 | 10/2009 | DeBelser et al. |
| 2009/0275886 A1 | 11/2009 | Blomquist et al. |
| 2009/0281393 A1 | 11/2009 | Smith |
| 2010/0008795 A1 | 1/2010 | DiPerna |
| 2010/0010330 A1 | 1/2010 | Rankers et al. |
| 2010/0010647 A1 | 1/2010 | Schroeder et al. |
| 2010/0030045 A1 | 2/2010 | Gottlieb et al. |
| 2010/0030387 A1 | 2/2010 | Sen |
| 2010/0057043 A1 | 3/2010 | Kovatchev et al. |
| 2010/0069730 A1 | 3/2010 | Bergstrom et al. |
| 2010/0069890 A1 | 3/2010 | Graskov et al. |
| 2010/0081993 A1 | 4/2010 | O'Connor |
| 2010/0094110 A1 | 4/2010 | Heller et al. |
| 2010/0095229 A1 | 4/2010 | Dixon et al. |
| 2010/0100037 A1 | 4/2010 | Cozmi et al. |

(56) References Cited

U.S. PATENT DOCUMENTS

| | | |
|---|---|---|
| 2010/0105999 A1 | 4/2010 | Dixon et al. |
| 2010/0107103 A1 | 4/2010 | Wallaert et al. |
| 2010/0121169 A1 | 5/2010 | Petisce et al. |
| 2010/0121170 A1 | 5/2010 | Rule |
| 2010/0125241 A1 | 5/2010 | Prud'Homme et al. |
| 2010/0130933 A1 | 5/2010 | Holland et al. |
| 2010/0138197 A1 | 6/2010 | Sher |
| 2010/0145276 A1 | 6/2010 | Yodfat et al. |
| 2010/0164727 A1 | 7/2010 | Bazargan et al. |
| 2010/0168711 A1 | 7/2010 | Bazargan et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185175 A1 | 7/2010 | Kamen et al. |
| 2010/0198034 A1 | 8/2010 | Thomas et al. |
| 2010/0198142 A1 | 8/2010 | Sloan et al. |
| 2010/0198183 A1 | 8/2010 | Lanigan et al. |
| 2010/0222765 A1 | 9/2010 | Blomquist et al. |
| 2010/0228186 A1 | 9/2010 | Estes et al. |
| 2010/0234707 A1 | 9/2010 | Goode, Jr. et al. |
| 2010/0253768 A1 | 10/2010 | El-Maraghi et al. |
| 2010/0261987 A1 | 10/2010 | Kamath et al. |
| 2010/0262117 A1 | 10/2010 | Magni et al. |
| 2010/0262434 A1 | 10/2010 | Shaya |
| 2010/0274592 A1 | 10/2010 | Nitzan et al. |
| 2010/0274751 A1 | 10/2010 | Blomquist |
| 2010/0286601 A1 | 11/2010 | Yodfat et al. |
| 2010/0292634 A1 | 11/2010 | Kircher, Jr. et al. |
| 2010/0295686 A1 | 11/2010 | Sloan et al. |
| 2010/0298685 A1 | 11/2010 | Hayter et al. |
| 2010/0305421 A1 | 12/2010 | Ow-Wing |
| 2010/0312085 A1 | 12/2010 | Andrews et al. |
| 2010/0317950 A1 | 12/2010 | Galley et al. |
| 2010/0323431 A1 | 12/2010 | Rutkowski et al. |
| 2010/0324382 A1 | 12/2010 | Cantwell et al. |
| 2010/0324398 A1 | 12/2010 | Tzyy-Ping |
| 2010/0331651 A1 | 12/2010 | Groll |
| 2011/0006876 A1* | 1/2011 | Moberg ............ A61M 5/16831 340/3.1 |
| 2011/0009725 A1 | 1/2011 | Hill et al. |
| 2011/0009813 A1 | 1/2011 | Rankers |
| 2011/0015509 A1 | 1/2011 | Peyser |
| 2011/0040247 A1 | 2/2011 | Mandro et al. |
| 2011/0040251 A1 | 2/2011 | Blomquist et al. |
| 2011/0047499 A1 | 2/2011 | Mandro et al. |
| 2011/0053121 A1 | 3/2011 | Heaton |
| 2011/0054390 A1 | 3/2011 | Searle et al. |
| 2011/0054391 A1 | 3/2011 | Ward et al. |
| 2011/0056264 A1 | 3/2011 | Kaplan et al. |
| 2011/0058485 A1 | 3/2011 | Sloan |
| 2011/0071765 A1 | 3/2011 | Yodfat et al. |
| 2011/0082439 A1 | 4/2011 | Wenger et al. |
| 2011/0092788 A1 | 4/2011 | Long et al. |
| 2011/0098548 A1 | 4/2011 | Budiman et al. |
| 2011/0106011 A1 | 5/2011 | Cinar et al. |
| 2011/0106050 A1 | 5/2011 | Yodfat et al. |
| 2011/0112478 A1 | 5/2011 | Gregor et al. |
| 2011/0112505 A1 | 5/2011 | Starkweather et al. |
| 2011/0112506 A1 | 5/2011 | Starkweather et al. |
| 2011/0118699 A1 | 5/2011 | Yodfat et al. |
| 2011/0124996 A1 | 5/2011 | Reinke et al. |
| 2011/0125095 A1 | 5/2011 | Lebel et al. |
| 2011/0130746 A1 | 6/2011 | Budiman |
| 2011/0137239 A1 | 6/2011 | Debelser et al. |
| 2011/0144569 A1 | 6/2011 | Britton et al. |
| 2011/0144586 A1 | 6/2011 | Michaud et al. |
| 2011/0152770 A1* | 6/2011 | DiPerna .................. F16J 15/32 604/151 |
| 2011/0166875 A1 | 7/2011 | Hayter et al. |
| 2011/0178462 A1 | 7/2011 | Moberg et al. |
| 2011/0178717 A1 | 7/2011 | Goodnow et al. |
| 2011/0184342 A1 | 7/2011 | Pesach et al. |
| 2011/0190694 A1 | 8/2011 | Lanier, Jr. et al. |
| 2011/0193704 A1* | 8/2011 | Harper ..................... A61B 5/14 340/505 |
| 2011/0196213 A1 | 8/2011 | Thukral et al. |
| 2011/0201911 A1 | 8/2011 | Johnson et al. |
| 2011/0208155 A1 | 8/2011 | Palerm et al. |
| 2011/0213225 A1 | 9/2011 | Bernstein et al. |
| 2011/0256848 A1* | 10/2011 | Bok ........................ G06F 3/048 455/411 |
| 2011/0257895 A1 | 10/2011 | Brauker et al. |
| 2011/0266999 A1 | 11/2011 | Yodfat et al. |
| 2011/0320130 A1 | 12/2011 | Valdes et al. |
| 2012/0013625 A1 | 1/2012 | Blomquist et al. |
| 2012/0013802 A1 | 1/2012 | Blomquist et al. |
| 2012/0029708 A1 | 2/2012 | Miller et al. |
| 2012/0029941 A1 | 2/2012 | Malave et al. |
| 2012/0030610 A1 | 2/2012 | DiPerna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0084728 A1 | 4/2012 | Huang et al. |
| 2012/0095315 A1 | 4/2012 | Tenbarge et al. |
| 2012/0096451 A1 | 4/2012 | Tenbarge et al. |
| 2012/0123230 A1 | 5/2012 | Brown et al. |
| 2012/0163481 A1 | 6/2012 | Ebner et al. |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0330227 A1 | 12/2012 | Budiman et al. |
| 2013/0012917 A1 | 1/2013 | Miller et al. |
| 2013/0036377 A1* | 2/2013 | Colley ............ H04M 1/724634 715/764 |
| 2013/0053816 A1 | 2/2013 | DiPerna et al. |
| 2013/0131630 A1 | 5/2013 | Blomquist |
| 2013/0151611 A1 | 6/2013 | Graham et al. |
| 2013/0162426 A1 | 6/2013 | Wiesner et al. |
| 2013/0172710 A1 | 7/2013 | Mears |
| 2013/0283196 A1 | 10/2013 | Farnan et al. |
| 2013/0298024 A1 | 11/2013 | Rhee et al. |
| 2013/0324928 A1 | 12/2013 | Kruse |
| 2013/0331790 A1 | 12/2013 | Brown et al. |
| 2013/0332388 A1 | 12/2013 | Martell et al. |
| 2013/0332874 A1 | 12/2013 | Rosinko et al. |
| 2014/0012511 A1* | 1/2014 | Mensinger ........... A61B 5/4839 702/19 |
| 2014/0039455 A1 | 2/2014 | Miller |
| 2014/0054883 A1 | 2/2014 | Lanigan et al. |
| 2014/0066890 A1 | 3/2014 | Sloan et al. |
| 2014/0074059 A1 | 3/2014 | Howell et al. |
| 2014/0137641 A1 | 5/2014 | Brown |
| 2014/0171772 A1 | 6/2014 | Blomquist |
| 2014/0187890 A1 | 7/2014 | Mensinger et al. |
| 2014/0200426 A1* | 7/2014 | Taub .................. A61B 5/14532 600/347 |
| 2014/0213977 A1 | 7/2014 | Miller |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276556 A1 | 9/2014 | Saint et al. |
| 2014/0276574 A1 | 9/2014 | Saint |
| 2014/0300490 A1 | 10/2014 | Kotz |
| 2014/0350371 A1 | 11/2014 | Blomquist et al. |
| 2014/0374275 A1 | 12/2014 | Morales et al. |
| 2014/0378898 A1 | 12/2014 | Rosinko |
| 2015/0045641 A1 | 2/2015 | Rule |
| 2015/0073337 A1 | 3/2015 | Saint et al. |
| 2015/0089369 A1 | 3/2015 | Ahn |
| 2015/0174320 A1 | 6/2015 | Grant |
| 2015/0205930 A1 | 7/2015 | Shaanan et al. |
| 2015/0350861 A1 | 12/2015 | Soli et al. |
| 2016/0030669 A1 | 2/2016 | Harris et al. |

(56) References Cited

U.S. PATENT DOCUMENTS

| | | |
|---|---|---|
| 2016/0082188 A1 | 3/2016 | Blomquist et al. |
| 2016/0098848 A1 | 4/2016 | Zamanakos et al. |
| 2016/0103887 A1 | 4/2016 | Fletcher et al. |
| 2016/0113594 A1 | 4/2016 | Koehler et al. |
| 2016/0119210 A1 | 4/2016 | Koehler et al. |
| 2016/0121047 A1 | 5/2016 | Kruse et al. |
| 2016/0199571 A1 | 7/2016 | Rosinko et al. |
| 2016/0228041 A1 | 8/2016 | Heller et al. |
| 2016/0271325 A1 | 9/2016 | Farnan et al. |
| 2016/0328991 A1 | 11/2016 | Simpson et al. |
| 2017/0000943 A1 | 1/2017 | Blomquist et al. |
| 2017/0056590 A1 | 3/2017 | DiPerna et al. |
| 2017/0134878 A1 | 5/2017 | Loychik et al. |
| 2017/0351842 A1 | 12/2017 | Booth et al. |
| 2018/0021514 A1 | 1/2018 | Rosinko |
| 2018/0042559 A1 | 2/2018 | Cabrera, Jr. et al. |
| 2018/0092578 A1 | 4/2018 | Blomquist |
| 2018/0137252 A1 | 5/2018 | Mairs et al. |
| 2018/0137938 A1 | 5/2018 | Vaddiraju et al. |
| 2018/0336208 A1 | 11/2018 | Kim |
| 2018/0361060 A9 | 12/2018 | Rosinko |
| 2019/0022314 A1 | 1/2019 | Schmidt et al. |
| 2019/0121506 A1 | 4/2019 | Matikyan |
| 2019/0125969 A1 | 5/2019 | Montgomery et al. |
| 2019/0167902 A1 | 6/2019 | Kamen et al. |
| 2019/0183434 A1 | 6/2019 | Sjolund et al. |
| 2019/0259485 A1 | 8/2019 | Blomquist et al. |
| 2019/0321552 A1 | 10/2019 | Diperna et al. |
| 2019/0328967 A1 | 10/2019 | Blomquist |
| 2019/0350501 A1 | 11/2019 | Blomquist et al. |
| 2019/0365997 A1 | 12/2019 | Harris |
| 2019/0388015 A1 | 12/2019 | Blomquist |
| 2020/0012401 A1 | 1/2020 | Rosinko et al. |
| 2020/0016335 A1 | 1/2020 | Diperna et al. |
| 2020/0114076 A1 | 4/2020 | Ulrich et al. |

FOREIGN PATENT DOCUMENTS

| | | | |
|---|---|---|---|
| DE | 19819407 A1 | 11/1999 | |
| DE | 10121317 A1 | 11/2002 | |
| DE | 10352456 A1 | 7/2005 | |
| EP | 1102194 A2 | 5/2001 | |
| EP | 1571582 A2 | 9/2005 | |
| JP | 2006034323 A | 2/2006 | |
| WO | WO-0045696 A1 | 8/2000 | |
| WO | WO-0074753 A1 | 12/2000 | |
| WO | WO-0152727 A1 | 7/2001 | |
| WO | WO-02062212 A2 | 8/2002 | |
| WO | WO-03082091 A2 | 10/2003 | |
| WO | WO-2005046559 A2 | 5/2005 | |
| WO | WO-2006061169 A1 | 6/2006 | |
| WO | WO-2006127841 A2 | 11/2006 | |
| WO | WO-2007000425 A2 | 1/2007 | |
| WO | WO-2007056592 A2 | 5/2007 | |
| WO | WO-2007089537 A1 | 8/2007 | |
| WO | WO-2007149533 A2 | 12/2007 | |
| WO | WO-2008048556 A2 | 4/2008 | |
| WO | WO-2008048582 A1 | 4/2008 | |
| WO | WO-2008048583 A1 | 4/2008 | |
| WO | WO-2008048584 A1 | 4/2008 | |
| WO | WO-2008048585 A1 | 4/2008 | |
| WO | WO-2008048586 A1 | 4/2008 | |
| WO | WO-2008048587 A1 | 4/2008 | |
| WO | WO-2008091320 A2 | 7/2008 | |
| WO | WO-2008112078 A2 | 9/2008 | |
| WO | WO-2008153689 A1 | 12/2008 | |
| WO | WO-2008153819 A1 | 12/2008 | |
| WO | WO-2009016636 A2 | 2/2009 | |
| WO | WO-2009032400 A1 | 3/2009 | |
| WO | WO-2009035753 A2 | 3/2009 | |
| WO | WO-2009035759 A1 | 3/2009 | |
| WO | WO-2009035761 A2 | 3/2009 | |
| WO | WO-2009035762 A2 | 3/2009 | |
| WO | WO-2009088983 A2 | 7/2009 | |
| WO | WO-2009089028 A2 | 7/2009 | |
| WO | WO-2009089029 A2 | 7/2009 | |
| WO | WO-2010111505 A2 * | 9/2010 | ............ A61M 5/142 |
| WO | WO-2011014704 A2 | 2/2011 | |
| WO | WO-2011068648 A2 | 6/2011 | |
| WO | WO-2013016363 A2 | 1/2013 | |
| WO | WO-2013184896 A1 | 12/2013 | |

OTHER PUBLICATIONS

Application and File History for U.S. Appl. No. 15/072,408, filed Mar. 17, 2016, Inventors Rosinko, et al.

Ballinger B., "Do You Really Need 10,000 Steps a Day?," May 30, 2016, retrieved from https://blog.cardiogr.am/do-you-really-need-10-000-steps-a-day-ce1c006b5d0a, on Jul. 18, 2019, 1 page.

Bott, et al., "Impact of Smoking on the Metabolic Action of Subcutaneous Regular Insulin in Type 2 Diabetic Patients," Horm. Metab. Res., vol. 37, 2005, pp. 445-449.

Ceglys G., "Risk Assessment Report on Dribble," Aug. 17, 2018, retrieved from https://dribbble.com/shots/4967551-Risk-Assessment-Report, on Jul. 26, 2019, 2 pages.

Chase, et at., "The Use of Insulin Pumps With Meal Bolus Alarms in Children With Type 1 Diabetes to Improve Glycemic Control," Diabetes Carem, vol. 29, No. 5, May 2006, pp. 1012-1015.

"Compare Insulin Pump for Diabetes," Printed from www.diabetesnet.com/diabetes-technology/insulin-pump-models.php, Jun. 18, 2009, 4 pages.

"Croissant, Pretzel and Bread Icons," Apr. 27, 2017, retrieved from https://www.shutterstock.com/image-vector/croissant-pretzel-bread-icons-cupcake-cake-397645378, 2017, 2 pages.

Dexcom, "Continuous Glucose Monitoring," Jun. 20, 2018, retrieved from https://www.dexcom.com/faq/app-g5-mobile-ios-faq, on Jul. 28, 2019, 3 pages.

Esposito A., "Implantable Glucose Sensor Featuring IDT Sensing Technology Awarded CE Mark," Jun. 22, 2016, retrieved from https://www.medicaldesignandoutsourcing.com/implantable-glucose-sensor-featuring-idt-sensing-technology-awarded-ce-mark/, on Jul. 28, 2019, 1 page.

Examination Report for EP Application No. 14775822.1, mailed on Dec. 12, 2019, 4 pages.

Examination Report for EP Application No. 14775822.1, mailed on Jan. 4, 2019, 4 pages.

Extended European Search Report for Application No. 14775822.1, mailed on Nov. 21, 2016, 9 pages.

Glum R., "Getting Started With Your Body+ Smart Scale," Withings, Jan. 28, 2016, retrieved from https://blog.withings.com/2016/01/28/getting-started-nokia-body-plus/, on Jul. 26, 2019, 3 pages.

Hoskins M., "What's Next in Diabetes Tech For 2018?," Jan. 11, 2018, retrieved from https://www.healthline.com/diabetesmine/diabetes-technology-expectations-2018#1, on Jul. 31, 2019, 3 pages.

International Preliminary Report on Patentability for Application No. PCT/US2014/021109, mailed on Sep. 24, 2015, 9 pages.

International Search Report and Written Opinion for PCT Application No. PCT/US2014/021109 mailed on Jun. 5, 2014, 13 pages.

Iyengar V., "Connected: Diabetes Data Management Made Easy," Aug. 2015, retrieved from https://endocrinenews.endocrine.org/august-2015-connected-diabetes-data-management-made-easy/, on Jul. 26, 2019, 2 pages.

Lehmann, et al., "Combining rule-based reasoning and mathematical modeling in diabetes care," Artificial Intelligence in Medicine, vol. 6, 1994, pp. 137-160.

Lovett L., "Dexcom's Integrated CGM Receives FDA Nod," Mar. 28, 2018, retrieved from https://www.mobihealthnews.com/content/dexcoms-integrated-cgm-receives-fda-nod, on Jul. 28, 2019, 1 page.

"Natural Icons Set," Jun. 21, 2017, retrieved from https://www.shutterstock.com/image-vector/natural-icons-set-16-filled-such-621208148, 2017, 3 pages.

Hildebrandt P, "Subcutaneous Absorption of Insulin in Insulin—Dependent Diavetic patients. Influence of Species Physico-Chemical properties of Insulin and Physiological factors," Danish Medical Bulletin, Aug. 1991, 10 pages.

Office Action mailed Apr. 4, 2018 for European Application No. 14775822.1, 4 pages.

(56) References Cited

OTHER PUBLICATIONS

Plougmann, et al., "DiasNet—a diabetes advisory system for communication and education via the internet," International Journal of Medical Informatics, vol. 64, 2001, pp. 319-330.

Puckett, et al., "A model for multiple subcutaneous insulin injections developed from individual diabetic patient data," vol. 269, 1995, p. E1115-E1124.

Ryan E., et al., "What's Next from Tandem? Predictive Low Glucose Suspend Under FDA Review," Mar. 28, 2018, retrieved from https://diatribe.org/whats-next-tandem-predictive-low-glucose-suspend-under-fda-review, on Jul. 26, 2019, 2 pages.

Smith Medical Md Inc., "Deltec Cozmo, Personalized Insulin Pump, Starting Guide," http://web.archive.org/web/20041207133223/http://www.cozmore.com/Library/-upload/starting.sub.--guide.sub.--032004.pdf, XP002497833, Dec. 7, 2004, pp. 1-83.

Stapel E., "Converting Between Decimals, Fractions, and Percents," Purplemath, 2006, 9 pages, Available at http://www.purplemath.com/modules/percents2.htm, 2006.

"Tandem Diabetes Care, Inc.—Form S-1," Jan. 16, 2018, retrieved from http://getfilings.com/sec-filings/180116/TANDEM-DIABETES-CARE-INC_S-1/, 2 pages.

Taryn, "Tidepool: Cool New App," Mar. 22, 2016, retrieved from https://forum.tudiabetes.org/t/tidepool-cool-new-app-for-analyzing-blood-sugartrends-thats-somuch-better-than-the-reports-i-get-with-my-pump/51854/10, on Jul. 26, 2019, 1 page.

Trajanoski, et al., "Pharmacokinetic Model for the Absorption of Subcutaneously Injected Soluble Insulin and Monomeric Insulin Analogues," Biomedizinische Technik, vol. 38, No. 9. Sep. 1, 1993, pp. 224-231.

Tran J., et al., "Smartphone-Based Glucose Monitors and Applications in the Management of Diabetes: An Overview of 10 Salient "Apps" and a Novel Smartphone-Connected Blood Glucose Monitor," Clinical Diabetes, retrieved from https://clinical.diabetesjournals.org/content/30/4/173, on Jan. 14, 2020, vol. 30 (4), Oct. 2012, pp. 173-178.

Wach, et al., "Numerical Approximation of Mathematical Model for Absorption of Subcutaneously Injected Insulin," Med & Biol. Eng & comput., vol. 33, 1995, pp. 18-23.

Walsh, et al., "Diabetes Technology—Concept 1: Super Bolus," available at Diabetes Technology—Concept 1: Super Bolus available at http://www.diabetesnet.com/diabetes.sub.--technology/super.sub.--bolus.ph-p>, Sep. 17, 2007, 3 pages.

Walsh J., et al., "Select & Test Your Correction Factor," Pumping Insulin, Fourth Edition, Chapter 13, 2006, 10 Pages.

Walsh J., et al., "Pumping Insulin: Everything you need for Success on a Smart insulin Pump," Torrey Pines Press, San Diego, ISBN 1-884804-86-1, 2006, 3 pages.

Wikipedia.com, "Wikipedia's definition for "basal rate"," printed from wikipedia.com on Jun. 12, 2009, 1 page.

Wilinska, et al., "Insulin Kinetics in Type-1 Diabetes: Continuous and Bolus Delivery of Rapid Acting Insulin," IEEE Transactions on Biomedical Engineering, vol. 52, No. 1, Jan. 2005, pp. 3-12.

Wills E., "Graphic Designer's Tube Maps Reveal Exactly How Far Underground You are on Every Station Platform," Jun. 22, 2018, retrieved from https://www.standard.co.uk/news/transport/graphic-designers-tube-maps-reveal-exactly-how-far-underground-you-are-on-every-station-platform-a3870156.html, on Jul. 28, 2019, 5 pages.

\* cited by examiner

SYSTEM AND METHOD FOR INTEGRATION AND DISPLAY OF DATA OF INSULIN PUMPS AND CONTINUOUS GLUCOSE MONITORING

RELATED APPLICATIONS

This application is a continuation of application Ser. No. 16/590,836, filed Oct. 2, 2019, now U.S. Pat. No. 11,607,492 issued Mar. 1, 2023, which is a continuation of application Ser. No. 15/072,408, filed Mar. 17, 2016, which is a continuation of application Ser. No. 13/800,453 filed Mar. 13, 2013, now U.S. Pat. No. 10,357,606 issued Jul. 23, 2019, each of which is hereby fully incorporated herein by reference.

FIELD OF THE INVENTION

The present invention relates to ambulatory infusions pumps and, more particularly, to integrating features of continuous glucose monitoring with insulin pumps.

BACKGROUND

There are many applications in academic, industrial, and medical fields that benefit from devices and methods that are capable of accurately and controllably delivering fluids, such as liquids and gases that have a beneficial effect when administered in known and controlled quantities. Such devices and methods can be particularly useful in the medical field where treatments for many patients include the administration of a known amount of a substance at predetermined intervals.

Insulin-injecting pumps have been developed for the administration of insulin for those suffering from both type I and type II diabetes. Recently, continuous subcutaneous insulin injection and/or infusion therapy with portable infusion devices has been adapted for the treatment of diabetes. Such therapy may include the regular and/or continuous injection or of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

Portable insulin pumps can be used in conjunction with continuous glucose monitoring (CGM) devices. A CGM provides a substantially continuous estimated blood glucose level through a transcutaneous sensor that measures analytes, such as glucose, in the patient's interstitial fluid rather than their blood. CGM systems typically consist of a transcutaneously-placed sensor, a transmitter and a monitor. A CGM system allows a patient or caregiver to insert a single sensor probe under the skin for multiple days. Thus, the patient is only required to perform a single moderately invasive action with a single entry point in the subdermal layer on, e.g., a weekly basis.

Ambulatory insulin infusion pumps typically allow the patient or caregiver to adjust the amount of insulin delivered, by a basal rate or a bolus, based on blood glucose data obtained by a blood glucose meter or CGM. Some ambulatory insulin infusion pumps may include the capability to interface with a blood glucose meter (BGM) or CGM such as, e.g., by receiving measured or estimated blood glucose levels and prompting the user to adjust the level of insulin being administered or planned for administration or, in cases of abnormally high blood glucose readings, prompting temporary cessation of insulin administration. These portable pumps may incorporate a BGM or CGM within the hardware of the pump or may communicate with a dedicated BGM or CGM via, wired or wireless data communication protocols. Such pumps may be particularly important in facilitating patient compliance and improved or more accurate treatment of diabetes. The delivery of insulin from a portable insulin pump making use of CGM data necessitates accurate and reliable CGM data output.

Generally, when CGM devices are used in conjunction with insulin pumps, the CGM device has a separate display from the insulin pump and the user must manually transfer data from the CGM to the pump in order for the pump to incorporate the data into its functioning. Even in instances where the pump can automatically receive CGM data, such as through a wireless connection, or incorporates the CGM in the pump, a user often must scroll through a number of screens of the pump to review the pump and CGM data and make a determination as to whether and how the data indicates that the user should activate the pump.

Therefore, there is a need for a system and a method for better integrating usage of CGM devices and data with insulin pumps.

SUMMARY OF THE INVENTION

A portable insulin pump can integrate and display data from a continuous glucose monitor (CGM) to allow a user to more readily determine whether any interaction with the pump is necessary. A screen of the pump, which can be a startup screen automatically displayed whenever the pump is turned on or activated from a sleep mode, can display a current glucose level of the user and historical glucose data obtained from the CGM as well as an estimate of the amount of un-metabolized insulin remaining in the user's body. This information allows the user to immediately assess whether any action needs to be taken with the pump, such as to deliver a bolus, without having to scroll through multiple pages and options to obtain the necessary information.

In an embodiment, a portable insulin pump includes a graphical user interface, a receiver adapted to receive information from a continuous glucose monitor and a processor functionally linked to the receiver and the graphical user interface. The processor can be configured to display a startup screen on the graphical user interface when the graphical user interface is activated from an inactive condition, such as being turned off or in sleep mode. The startup screen can display a current glucose level of a user and historical glucose level data based off of information received from the CGM at the receiver. The startup screen can also display an estimate of the amount of un-metabolized insulin remaining in the user's body.

In another embodiment, a portable insulin pump can integrate with a continuous glucose monitor to automatically calculate a recommended bolus for a user. When the user uses a blood sample to calibrate the CGM with an actual blood glucose reading, the CGM can automatically transmit that blood glucose value to the pump. The pump can then determine whether that value is above a threshold and, if so, automatically calculate a bolus of insulin to bring the user's blood glucose level below the threshold.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for integrating usage of ambulatory infusion pumps with continuous glucose monitoring devices. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1:
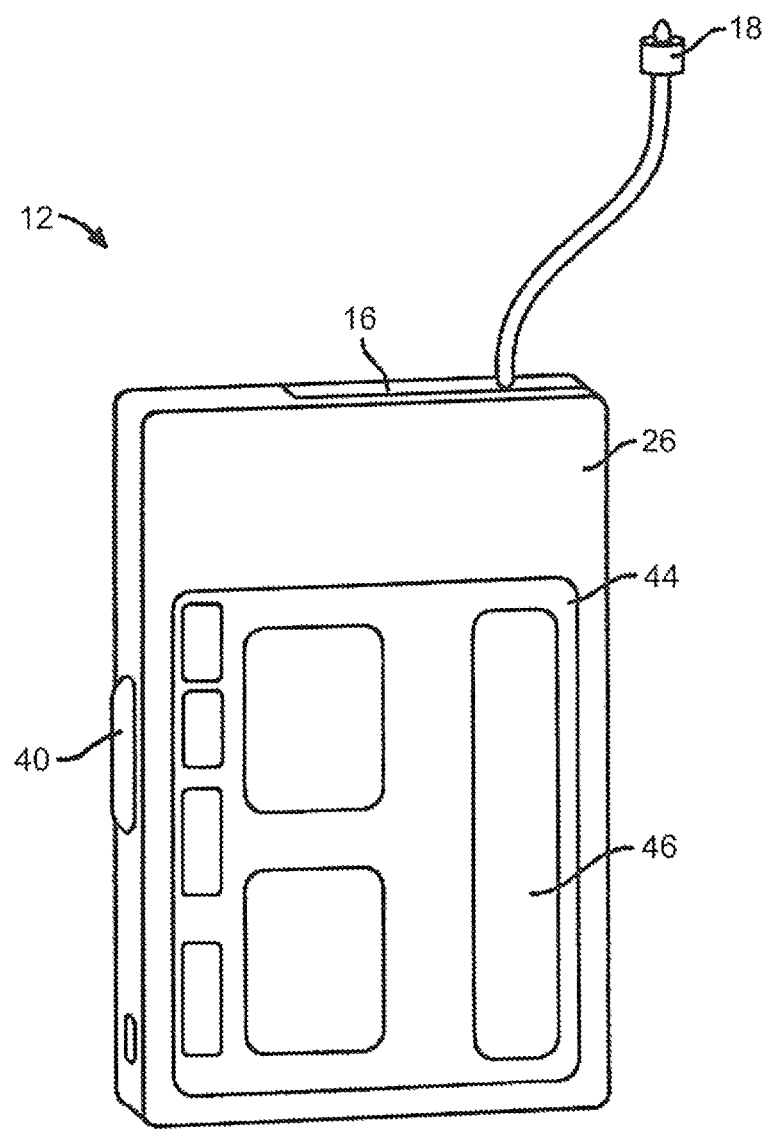
FIG. 1 is a perspective view of an infusion pump according to an embodiment of the present invention.

FIG. 1 depicts an embodiment of a pump 12 such as an infusion pump that can include an internal pumping or delivery mechanism and reservoir for delivering medicament such as insulin to a patient and an output/display 44. The type of output/display 44 may vary as may be useful for a particular application. The type of visual output/display may include LCD displays, LED displays, plasma displays, OLED displays and the like. The output/display 44 may also be an interactive or touch sensitive screen 46 having an input device such as, for example, a touch screen comprising a capacitive screen or a resistive screen. The pump 12 may additionally include a keyboard or other input device known in the art for data entry, which may be separate from the display. The output/display 44 of the pump 12 may also include a capability to operatively couple to a secondary display device such as a laptop computer, mobile communication device such as a smartphone or personal digital assistant (PDA) or the like. Further details regarding such pump devices can be found in U.S. Patent Application No. 2011/0144586, which is incorporated herein by reference.

Some embodiments of an infusion system may include a portable infusion device, as described above and a remote commander device. In such an instance, the portable infusion device may include a suitably configured receiver and/or transmitter for communication with an external device such as a remote commander, as well as programming for directing the use of the device; and the remote commander may additionally include a suitably configured receiver and/or transmitter for communication with an external device such as a portable infusion device, as well as programming for directing the use of the device. For instance, the remote commander may include one or more of the functionalities described herein with respect to the portable infusion device. In addition, some GUI embodiments may be available to a user by downloading a software application onto the user's cell phone and/or PDA, which would allow the user to use their cell phone or PDA as a remote commander to the portable infusion device.

Figure 2:
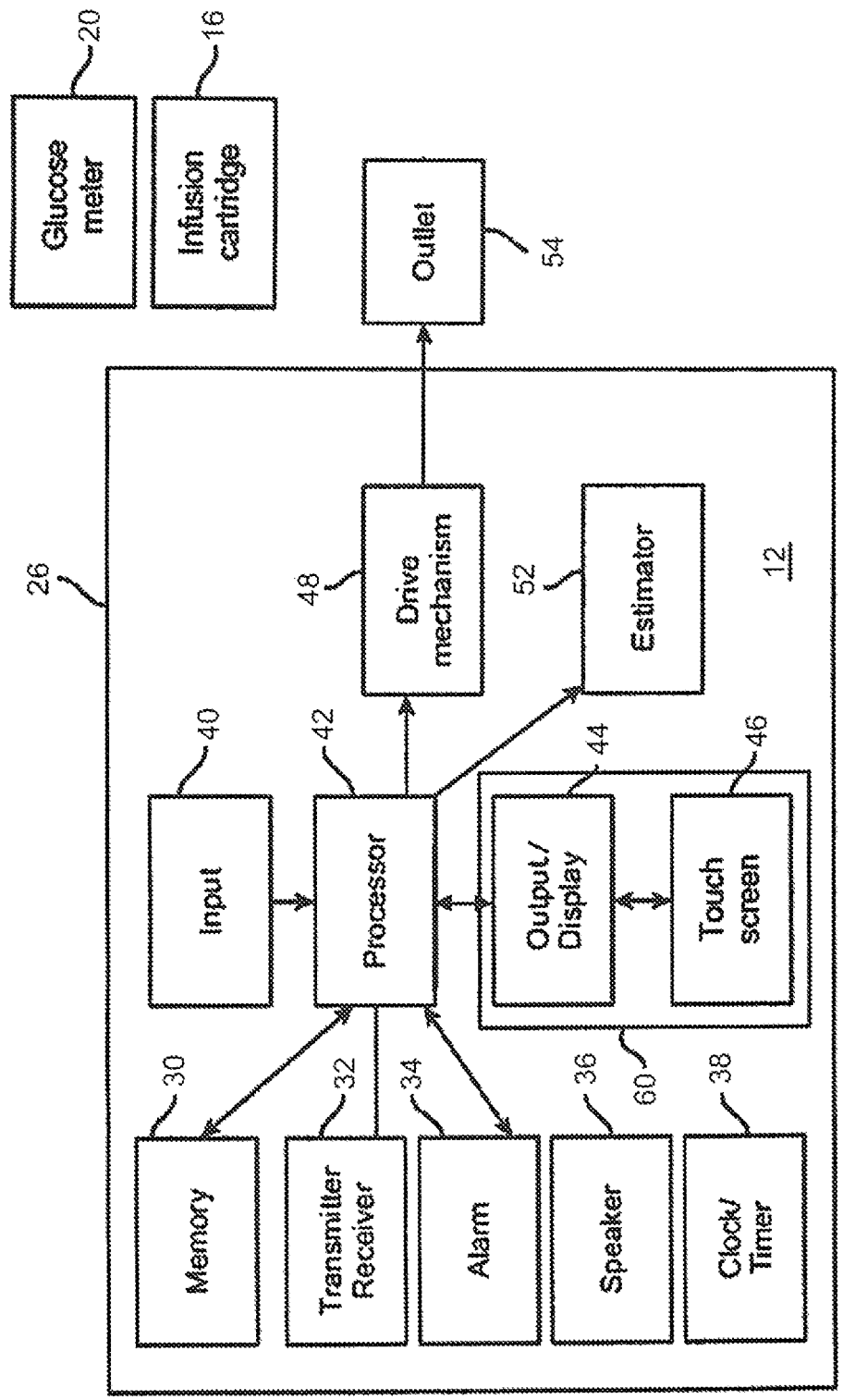
FIG. 2 is a block diagram representing an embodiment of an infusion pump.

FIG. 2 illustrates a block diagram of some of the features that may be incorporated within the housing 26 of the pump 12. The pump 12 includes a processor 42 that functions to control the overall functions of the device. The infusion pump 12 may also include a memory device 30, a transmitter/receiver 32, an alarm 34, a speaker 36, a clock/timer 38, an input device 40, the processor 42, a user interface suitable for accepting input and commands from a user such as a caregiver or patient, a drive mechanism 48, and an estimator device 52. One embodiment of a user interface as shown in FIG. 2 is a graphical user interface (GUI) 60 having a touch sensitive screen 46 with input capability. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump 12. The GUI 60 may be configured for displaying a request for the user to input data and for receiving user input data in response to the request, and communicating that data to the memory.

The processor 42 may communicate with and/or otherwise control the drive mechanism, output/display, memory, a transmitter/receiver and other components. In some embodiments, the processor 42 may communicate with a processor of another device, for example, a continuous glucose monitor (CGM), through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor that may sense pressure, temperature or other parameters. The processor 42 may determine the capacity of the drug delivery reservoir and/or the volume of fluid disposed in the drug delivery reservoir and may set therapeutic parameters based on its determination.

The processor 42 may also include additional programming to allow the processor 42 to learn user preferences and/or user characteristics and/or user history data. This information can be utilized to implement changes in use, suggestions based on detected trends, such as weight gain or loss. The processor can also include programming that allows the device to generate reports, such as reports based upon user history, compliance, trending, and/or other such data. Additionally, infusion pump device embodiments of the disclosure may include a "power off" or "suspend" function for suspending one or more functions of the device, such as suspending a delivery protocol, and/or for powering off the device or the delivery mechanism thereof. For some embodiments, two or more processors may be used for controller functions of the infusion pumps, including a high power controller and a low power controller used to maintain programming and pumping functions in low power mode, in order to save battery life.

The memory device 30 may be any type of memory capable of storing data and communicating that data to one or more other components of the device, such as the processor. The memory may be one or more of a Flash memory, SRAM, ROM, DRAM, RAM, EPROM and dynamic storage, for example. For instance, the memory may be coupled to the processor and configured to receive and store input data and/or store one or more template or generated delivery patterns. For example, the memory can be configured to store one or more personalized (e.g., user defined) delivery profiles, such as a profile based on a user's selection and/or grouping of various input factors, past generated delivery profiles, recommended delivery profiles, one or more traditional delivery profiles, e.g., square wave, dual square wave, basal and bolus rate profiles, and/or the like. The memory can also store, for example, user information, history of use, glucose measurements, compliance and an accessible calendar of events.

The housing 26 of the pump 12 may be functionally associated with an interchangeable and a removable glucose meter 20 and/or infusion cartridge 16. The infusion cartridge 16 may have an outlet port 54 that may be connected to an infusion set (not shown) via an infusion set connector 18. Further details regarding some embodiments of various infusion pumps can be found in U.S. Patent Application Publication No. 2011/0144586, which is hereby incorporated by reference.

Figure 3:
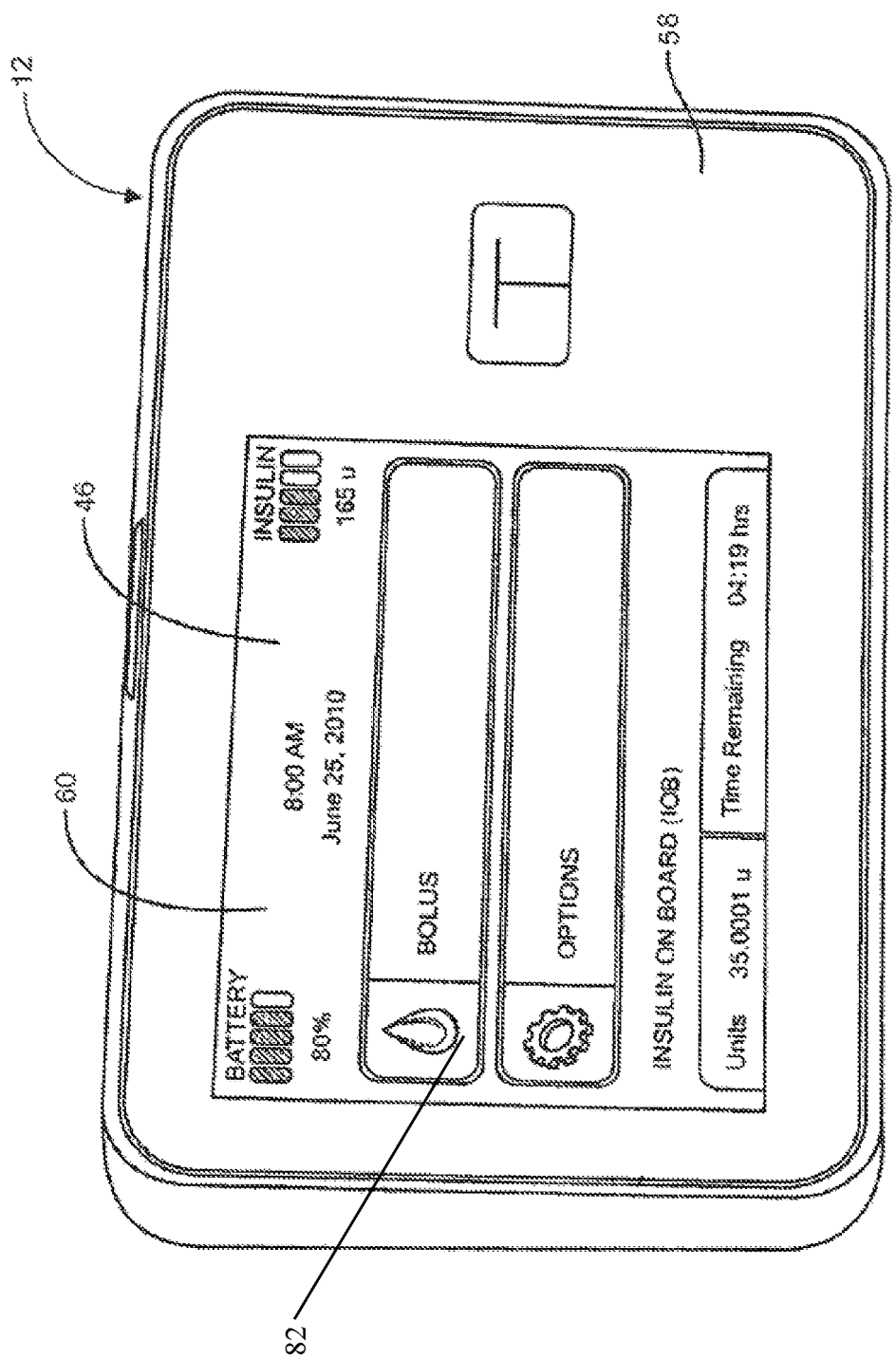
FIG. 3 depicts a screen shot of a home screen page of a graphical user interface of an infusion pump according to an embodiment of the present invention.

Referring to FIG. 3, a front view of the pump 12 is depicted. The pump 12 may include a user interface, such as, for example, a user-friendly GUI 60 on a front surface 58 or other convenient location of the pump 12. The GUI 60 may include a touch-sensitive screen 46 that may be configured for displaying data, facilitating data entry by a patient, providing visual tutorials, as well as other interface features that may be useful to the patient operating the pump 12. A bolus object 82 can also be displayed on the screen 46.

Figure 4:
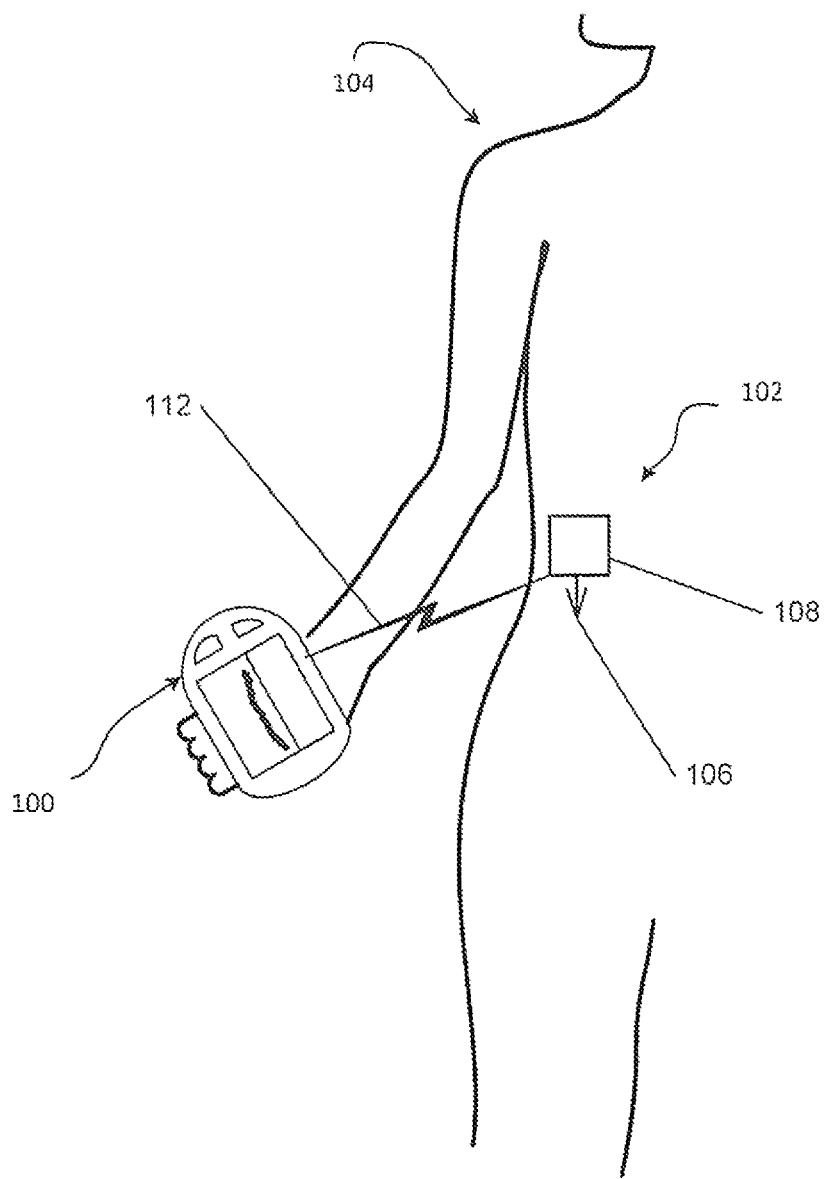
FIG. 4 is a partial schematic view depicting a continuous glucose monitor according to an embodiment of the present invention deployed on a patient.

Pump 12 can interface with a continuous glucose monitor (CGM) that provides a substantially continuous estimated glucose level through a transcutaneous sensor that measures analytes, such as glucose, in the patient's interstitial fluid rather than their blood. Referring to FIG. 4, a CGM system 100 according to an embodiment of the present invention is shown. The illustrated CGM system 100 includes a sensor 102 affixed to a patient 104 and is associated with the insulin infusion device 12. The sensor 102 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be calibrated with the patient's blood glucose (BG) level. The sensor 102 includes a sensor body 108 that transmits data associated with the interstitial fluid to which the sensor probe is exposed. The data may be transmitted from the sensor 102 to the glucose monitoring system 100 via a wireless transmitter, such as a near field communication (NFC) radio frequency (RF) transmitter or a transmitter operating according to a "WiFi" or "Bluetooth" protocol or the like, or the data may be transmitted via a wire connector from the sensor 102 to the monitor system 100. Transmission of sensor data to the glucose monitor system 100 by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In one embodiment, part of the CGM system 100 is incorporated into the pump 12 such that the processor 42 is adapted to receive the data from the sensor 102 and process and display the data on the display 44. In another embodiment, the CGM 100 is a separate device that communicates with the pump 12 through a wired or wireless link to transmit the CGM data to the pump 12.

Figure 5:
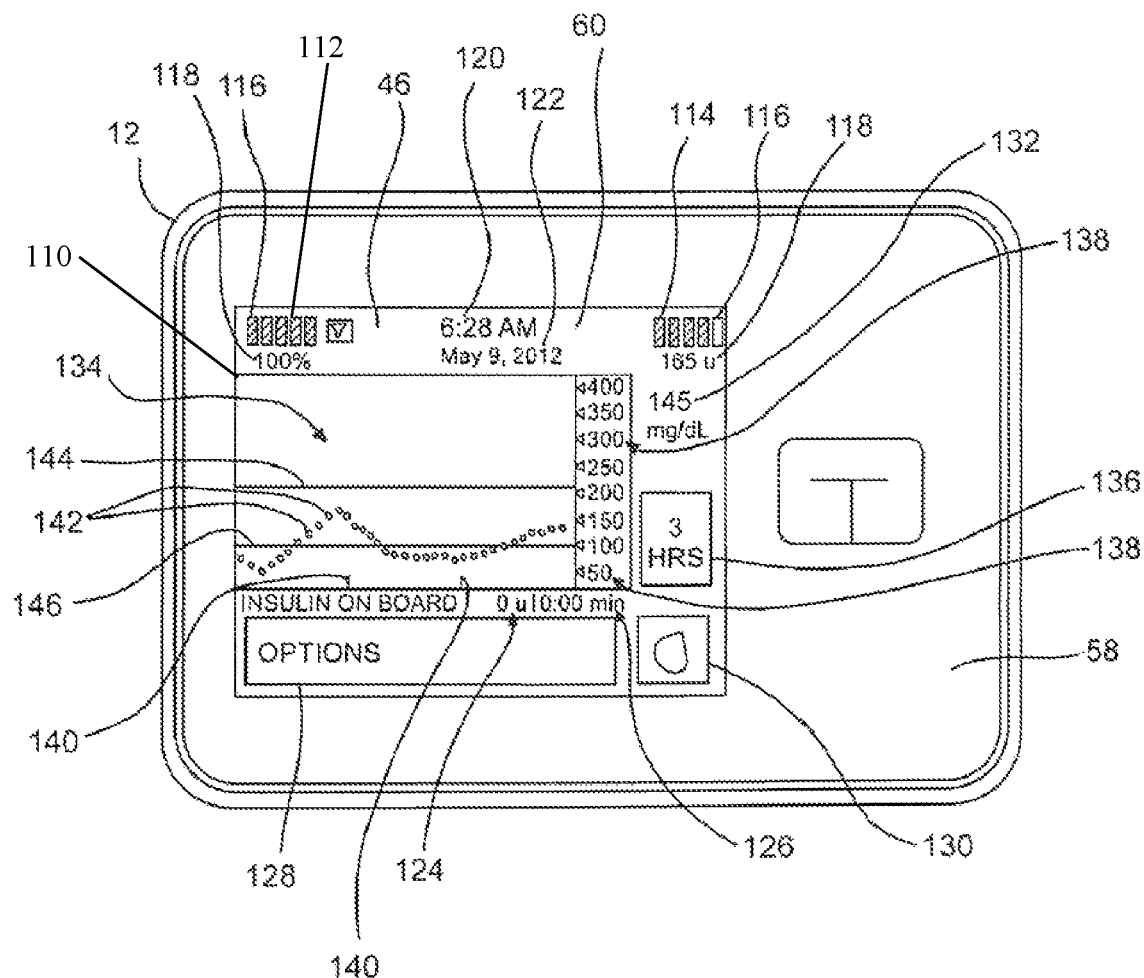
FIG. 5 depicts a screen shot of a screen page of a graphical user interface of an infusion pump according to an embodiment of the present invention.

Referring to FIG. 5, there can be seen a pump screen 110 incorporating pump 12 data and CGM data according to an embodiment of the present invention. Pump screen 110 can be displayed on the touch screen 46 of the GUI 60 on the front surface 58 of the pump 12. Screen 110 can include a battery life indicator 112 and an insulin indicator 114. Each indicator 112, 114 can include one or more of a graphical indication, shown in FIG. 4 as a plurality of indicator bars 116 and a textual indicator 118 such as a percentage or amount remaining. The time 120 and date 122 can also be displayed on screen 110. The screen 110 can also include an indication of the amount of insulin on board 124, that is, the amount of un-metabolized insulin already present in the user's body, as well as a time remaining object 126 counting down the amount of time the insulin on board is calculated to remain in the user's body. An options key 128 can allow a user to scroll through various pump operation options and a bolus object 130 can allow a user to begin programming a bolus of insulin.

With further reference to FIG. 5, information regarding the user's glucose level received from the CGM device can be incorporated and displayed on the pump screen 110 alongside insulin pump 12 data. The information can include the user's current glucose level 132 as well as a graphical representation 134 of historical glucose data that can be used, for example, to view glucose level trends and rates of change. A timeframe object 136 can be used to select a timeframe over which to view the historical data. The right side of the graph 134 can include a plurality of glucose values 138 forming the vertical axis of the graph 134. The horizontal axis of the graph 134 tracks the time period over which the data is displayed and can include hash marks 140 or other indicators, including numerical indicators, indicating equal divisions of the selected timeframe. The user's glucose level is therefore shown on the graph 134 as a function of time and can be shown as discrete points 142 as shown in FIG. 5. Alternatively, the glucose level versus time can be shown as a continuous line or curve. The graph 134 can also include a high glucose level indicator line 144 and a low glucose level indicator line 146 identifying predetermined patient specific thresholds that make it easy for a user to see when the user's glucose level has crossed a threshold. Although shown and described as being displayed in a graphical format, CGM data can also be displayed in a textual and numerical format on GUI 60 as well as audibly through, e.g., a speaker.

The pump screen 110 includes all data that the user needs to determine whether interaction with the pump is necessary. For example, for the user to determine whether or not to administer a bolus of insulin, the key information of the user's current glucose level 132, the amount of insulin on board 124 and historical glucose level data 144 indicating recent trends and rates of change is all displayed to the user on one convenient screen. In addition, whether underlying requirements for the pump to deliver a bolus are met, such as the battery life 112 of the pump and the amount of insulin 114 in the pump reservoir, can also be determined from the display of this information on the same screen 110.

The pump screen 110 shown in FIG. 5 can be a default or startup screen of the GUI 60. As a startup screen, pump screen 110 can be the first screen displayed on the GUI anytime the user powers the pump 12 on or activates the pump 12 from a sleep mode. This allows the user to immediately assess whether any action needs to be taken with the pump, such as to deliver a bolus, charge a battery or change a cartridge containing the insulin reservoir. The user can therefore take any necessary action with little more than a glance at the device, rather than having to scroll through multiple pages and options to determine whether action needs to be taken. In some embodiments, the pump 12 can also revert to the startup pump screen 110 whenever the GUI 60 has been inactive for a predetermined period of time and/or whenever a home key or home key sequence is entered.

Figure 6:
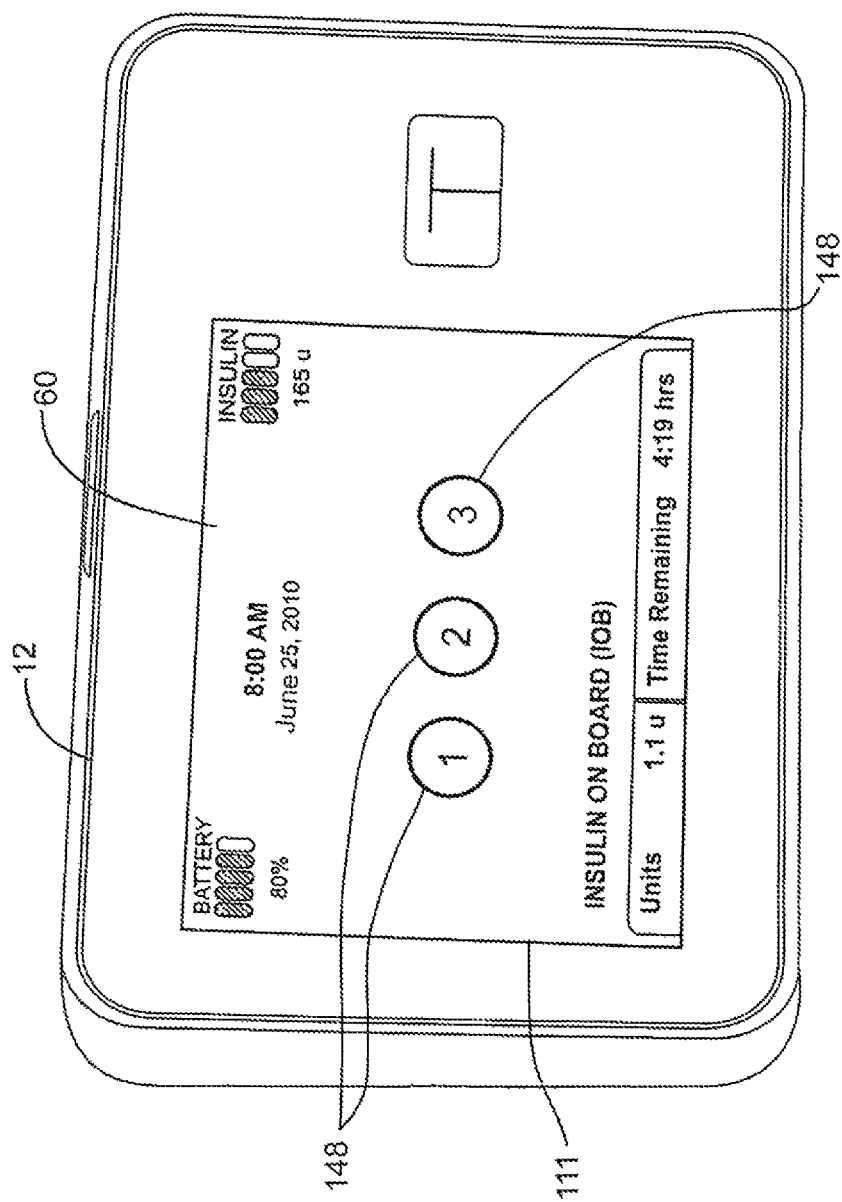
FIG. 6 depicts a screen shot of an unlock screen of a graphical user interface of an infusion pump according to an embodiment of the present invention.

If the user determines from the startup pump screen 110 that a bolus should be delivered, a deliver bolus command can also be begun directly from the screen 110 by selecting the deliver bolus object 130. If some other pump interaction is required, the user can access the necessary command with the options key 128. In some embodiments, before the user can deliver a bolus or otherwise change a pump parameter, the user must unlock the startup pump screen 110, such as by entering a specific numeric sequence or swiping along the touchscreen 46 in a specific manner. An unlock screen such as the unlock screen 111 shown in FIG. 6 can pop up over or in place of the startup pump screen 110 to provide for unlocking of the device. As shown in FIG. 6, in one embodiment unlock screen 111 includes a plurality of numerical indicators 148 with which the user enters a previously saved code to unlock the pump 12. Such an unlock procedure will prevent the user from accidentally altering pump operation when it is not intended. Aspects of these features are further explained in U.S. Provisional Patent Application Ser. No. 61/656,997 and in U.S. patent application Ser. No. 13/801,230 entitled "Preventing Inadvertent Changes in Ambulatory Medical Devices," filed Mar. 13, 2013 by M. Rosinko, et al., each of which is hereby incorporated by reference.

Because CGM devices estimate blood glucose levels from analyzing interstitial plasma or fluid rather than blood as with blood glucose monitors that utilize a sample of blood obtained from, e.g., a finger stick, CGM devices generally are not as well-suited for accurate blood glucose monitoring. Accordingly, CGMs are most often used for identifying trends in blood glucose levels over time and for providing estimates thereof. However, to ensure that a CGM device is estimating the user's glucose level as accurately as possible, such devices require a user to calibrate with an actual blood sample several times a day that is then used to compare the user's actual blood glucose level with the glucose levels measured by the CGM. Typically, after this is done the user must then manually enter the blood glucose data into the pump to allow therapy parameters to be calculated based on the data. Aspects of advanced calibration techniques that may be used in such systems are found in U.S. patent application Ser. No. 13/841,028 entitled "Predictive Calibration" to Saint, the entirety of which is incorporated by reference.

Figure 7:
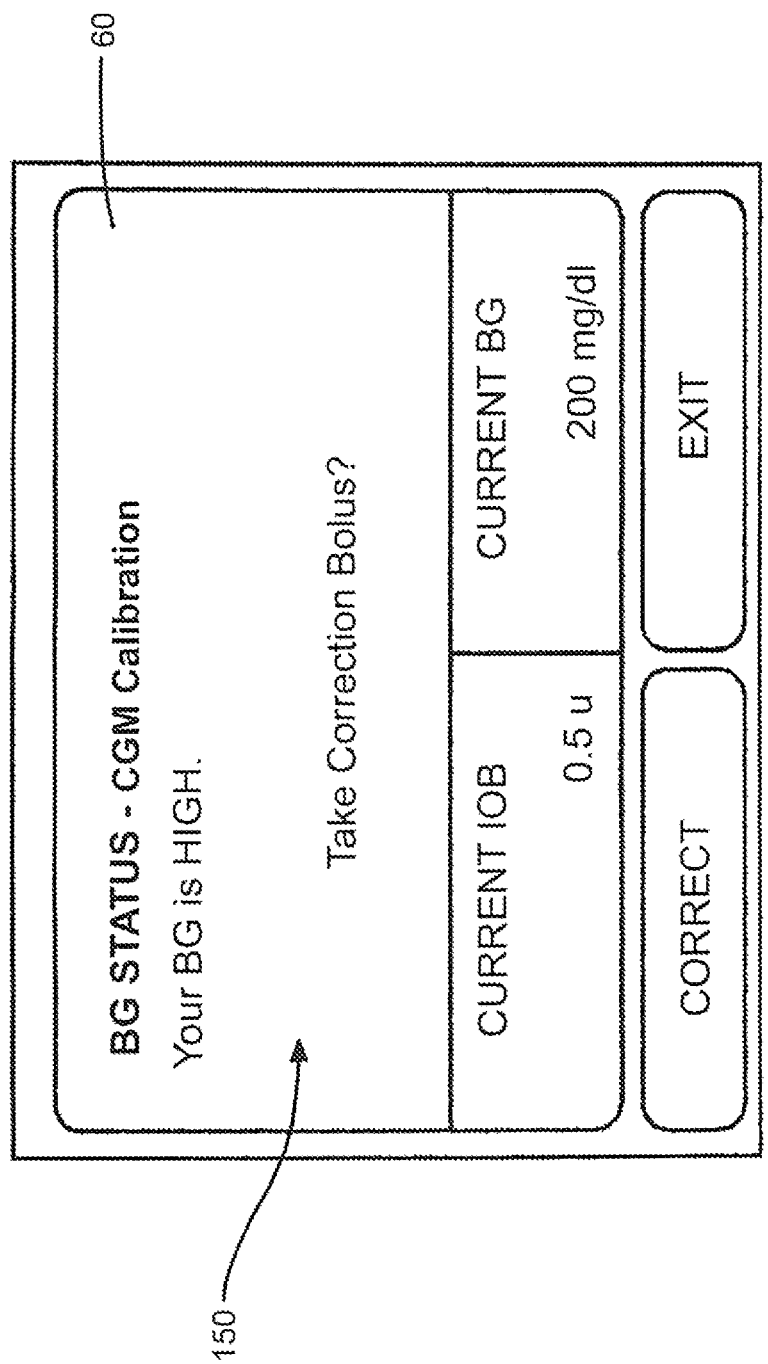
FIG. 7 depicts a screen shot of a bolus recommendation screen of a graphical user interface of an infusion pump according to an embodiment of the present invention.

However, in an embodiment of a pump 12 that communicates with a CGM and that integrates CGM data and pump data as described herein, the CGM can automatically transmit the blood glucose data determined from the calibration sample to the pump. The pump can then automatically determine therapy parameters based on the data. For example, if the calibration sample indicates that the user's blood glucose is over a high blood glucose threshold, the pump can automatically calculate an insulin bolus to bring the user's blood glucose below the threshold. In one embodiment, the pump presents the bolus to the user as a recommended bolus 150 on the GUI 60 that the user must approve in order for it to be delivered as shown in FIG. 7. In some embodiments, a visual, audible or tactile alarm, or some combination of these, can automatically be issued to alert the user to a suggested action and reason for the action, such as a high blood glucose reading and corresponding recommended bolus.

Figure 8:
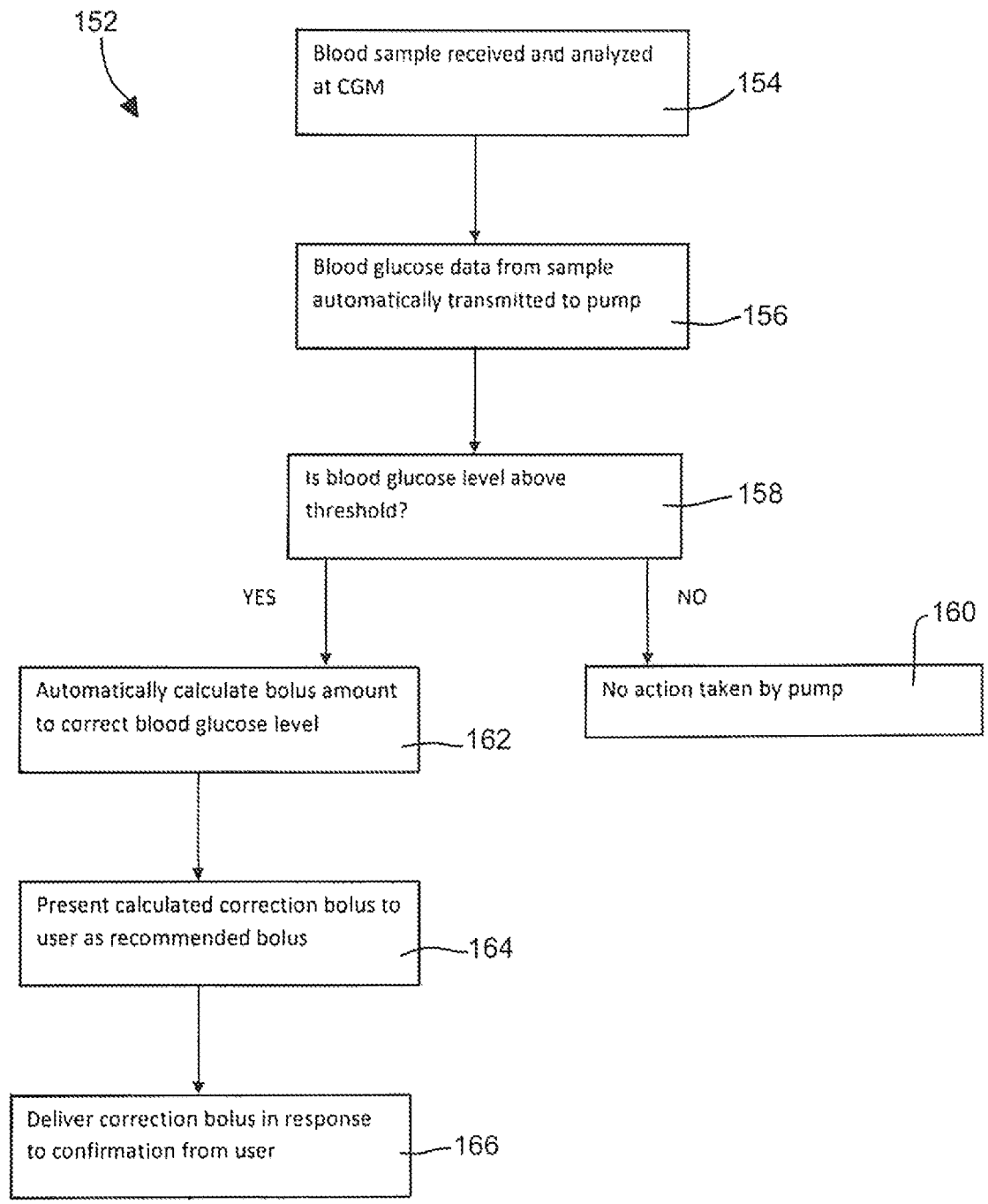
FIG. 8 is a flowchart of a method of recommending a correction bolus according to an embodiment of the present invention.

Referring now to FIG. 8, a flowchart of a method of recommending a correction bolus 152 is depicted. At step 154, a user submitted blood sample is received at the CGM for calibration purposes. The blood glucose level of the blood sample is determined and then automatically transmitted to the pump at step 156. The pump determines at step 158 whether the blood glucose level is above a patient specific threshold level. If it is not, at step 160 no action is taken by the pump. If the level is above the threshold, then at step 162 the pump automatically calculates a correction bolus and displays the correction bolus as a recommendation to the user at step 164. If the user confirms the recommended bolus, the bolus is delivered to the user by the pump at step 166.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method of displaying information to aid in providing diabetes therapy with a portable insulin pump, comprising:
    activating a graphical user interface of a portable insulin pump system from an inactive condition;
    displaying a startup screen on the graphical user interface automatically upon activating the graphical user interface, the startup screen including information relating to glucose levels of the user and a bolus delivery object selectable to initiate programming of a bolus delivery of insulin when the startup screen is not in a locked configuration,
    wherein displaying the startup screen on the graphical user interface automatically upon activating the graphical user interface includes displaying the startup screen in the locked configuration with the information relating to glucose levels visible but not touch-selectable on the startup screen to enable the user to assess whether any action needs to be taken with the portable insulin pump while the startup screen is in the locked configuration, and
    wherein the bolus delivery object on the startup screen is not selectable to initiate programming of a bolus delivery of insulin until the startup screen is unlocked from the locked configuration.

2. The method of claim 1, wherein the bolus delivery object is not visible on the startup screen when the startup screen is in the locked configuration.

3. The method of claim 1, further comprising displaying one or more unlock indicators on the startup screen and further comprising receiving user input via the unlock indicators to unlock the startup screen from the locked configuration.

4. The method of claim 3, wherein displaying one or more unlock indicators on the startup screen includes displaying the unlock indicators over the startup screen such that at least a portion of the startup screen is visible.

5. The method of claim 1, wherein displaying on the startup screen information relating to glucose levels includes displaying historical data in a graphical format depicting glucose levels of the user over time.

6. The method of claim 1, wherein displaying the startup screen further includes displaying at least one of a battery life indicator indicating a remaining life of a battery of the portable insulin pump and a reservoir level indicator indicating a remaining amount of insulin in an insulin reservoir of the portable insulin pump.

7. The method of claim 1, wherein activating the graphical user interface of a portable insulin pump from an inactive condition includes activating the graphical user interface from a sleep mode.

8. The method of claim 1, further comprising displaying the startup screen when no user input is received through the graphical user interface for a predetermined period of time.

9. The method of claim 1, wherein activating the graphical user interface of a portable insulin pump system and displaying the startup screen on the graphical user interface activates the graphical user interface and displays the startup screen on a display of the portable insulin pump.

10. The method of claim 1, wherein activating the graphical user interface of a portable insulin pump system and displaying the startup screen on the graphical user interface activates the graphical user interface and displays the startup screen on a display of a remote commander configured to control the portable insulin pump.

11. A portable insulin pump system, comprising:
    a graphical user interface; and
    a processor functionally linked to the graphical user interface to control display of information on the graphical user interface, wherein the processor is configured to automatically display a startup screen on the graphical user interface when the graphical user interface is activated from an inactive condition, the startup screen including information relating to glucose levels of the user and a bolus delivery object selectable to initiate a programming of a bolus delivery of insulin when the startup screen is not in a locked configuration,
    wherein the processor is configured to display the startup screen in the locked configuration with the information relating to glucose levels visible but not touch-selectable on the startup screen to enable the user to assess whether any action needs to be taken with the portable insulin pump while the startup screen is in the locked configuration, and wherein the bolus delivery object on the startup screen is not selectable to initiate programming of a bolus delivery of insulin until the startup screen is unlocked from the locked configuration.

12. The portable system of claim 11, wherein the processor is configured to display the startup screen with bolus delivery object not visible when the startup screen is in the locked configuration.

13. The portable insulin pump system of claim 11, wherein the processor is further configured to display one or more unlock indicators on the startup screen and receive user input via the unlock indicators to unlock the startup screen from the locked configuration.

14. The portable insulin pump system of claim 13, wherein the processor is further configured to display the unlock indicators over the startup screen such that at least a portion of the startup screen is visible.

15. The portable insulin pump system of claim 11, wherein the information relating to glucose levels includes historical data presented in a graphical format illustrating glucose levels of the user over time.

16. The portable insulin pump system of claim 11, further comprising a battery that powers the processor and a reservoir that contains insulin for delivery to the user, and the startup screen further includes at least one of a battery life indicator indicating a remaining life of the battery and a reservoir level indicator indicating a remaining amount of insulin in the reservoir.

17. The portable insulin pump system of claim 11, wherein activating the graphical user interface from an inactive condition includes activating the graphical user interface from a sleep mode.

18. The portable insulin pump system of claim 11, wherein the processor is further configured to display the startup screen when no commands have been entered into the graphical user interface for a predetermined period of time.

19. The portable insulin pump system of claim 11, further comprising a portable insulin pump, and wherein the graphical user interface is part of the portable insulin pump.

20. The portable insulin pump system of claim 11, further comprising a remote commander configured to control a portable insulin pump and the graphical user interface is part of the remote commander.

* * * * *